United States Patent
Samnick

(10) Patent No.: US 9,682,158 B2
(45) Date of Patent: *Jun. 20, 2017

(54) THERAPY OF MALIGNANT NEOPLASIAS

(75) Inventor: Samuel Samnick, Homburg/Saar (DE)

(73) Assignee: Samuel Samnick, Homburg/Saar (DE)

( * ) Notice: Subject to any disclaimer, the term of this patent is extended or adjusted under 35 U.S.C. 154(b) by 1565 days.

This patent is subject to a terminal disclaimer.

(21) Appl. No.: 11/602,463

(22) Filed: Nov. 20, 2006

(65) Prior Publication Data

US 2007/0128108 A1    Jun. 7, 2007

Related U.S. Application Data

(60) Provisional application No. 60/738,402, filed on Nov. 18, 2005.

(51) Int. Cl.
*A61K 51/04* (2006.01)

(52) U.S. Cl.
CPC ............................... *A61K 51/0402* (2013.01)

(58) Field of Classification Search
CPC ................................................ A61K 51/0402
USPC ............................. 424/1.11, 1.62, 1.69, 1.85
See application file for complete search history.

(56) References Cited

U.S. PATENT DOCUMENTS 5,019,323 A * 5/1991 Lambrecht et al. .......... 376/201

FOREIGN PATENT DOCUMENTS

WO    WO 2004/071505    * 8/2004 ........... A61K 31/198

OTHER PUBLICATIONS

Kersemans et al., J. Nuclear Med., 2005, 46(3), p. 532-539.*
Romeike, B. et al., Anticancer Research, Nov. 2004, 24(6), p. 3971-6.*
Yanik et al., J. Clin. Oncol., 2002, 20(8), p. 2142-9.*
Samnick, S. et al., Eur. J. Nuclear Medicine, 2000, 27(10), p. 1543-1551.*
Sisson et al., J. Nucl. Med., 1990, 31, p. 1479-1485.*
McLaughlin, W. et al., J Surg Oncol., 1988, 37(3), p. 192-7 (abstract).*
Chen, J. et al., Applied Radiation and Isotopes, 2004, 61(5), p. 887-891 (abstract).*
Samnick et al., Nucl. Med. Comm., 2002, 23, p. 121-130.*
Imahori et al., J. Nucl. Med., 1998, 39, p. 325-333.*
Matthay et al ., J. Nucl. Med., 2001, 42(11), p. 1713-21 (abstract).*
Imhof et al., "Response, Survival, and Long-Term Toxicity After Therapy With the Radiolabeled Somatostatin Analogue [90Y-DOTA]-TOC in Metastasized Neuroendocrine Cancers," *Journal of Clinical Oncology*, 29(17):2416-2423 (2011).
Iten et al., "Response to [90Yttrium-DOTA]-TOC Treatment is Associated with Long-term Survival Benefit in Metastasized Medullary Thyroid Cancer: A Phase II Clinical Trial," *Clin Cancer Res*, 13 (22), pp. 6696-6702 (2007).
Lassmann et al., "Dosimetry and Thyroid Cancer: The Individual Dosage of Radioiodine," *Endocrine-Related Cancer* 17, R161-R172 (2010).
Silberstein et al., "The SNMMI Practice Guideline for Therapy of Thyroid Disease with $^{131}$I 3.0," *The Journal of Nuclear Medicine*, 53(10):1633-1651 (2012).
Tabei et al., "Assessment of Radioiodine Clearance in Patients with Differentiated Thyroid Cancer," *Radiation Protection Dosimetry* pp. 1-5 (2012).
Woodrum et al., Role of $^{131}$I in the Treatment of Well Differentiated Thyroid Cancer, *Journal of Surgical Oncology*, 89:114-121 (2005).

* cited by examiner

*Primary Examiner* — Michael G Hartley
*Assistant Examiner* — Leah Schlientz
(74) *Attorney, Agent, or Firm* — Ropes & Gray LLP

(57) ABSTRACT

The present invention provides a method for the treatment of malignant neoplasias comprising the step of administering an L-phenylalanine conjugated to a beta- or alpha-emitting isotope to a subject in the need thereof. Moreover, the invention provides a method for the monitoring of the progress of such treatment of malignant neoplasias.

12 Claims, 18 Drawing Sheets

Figure 1:
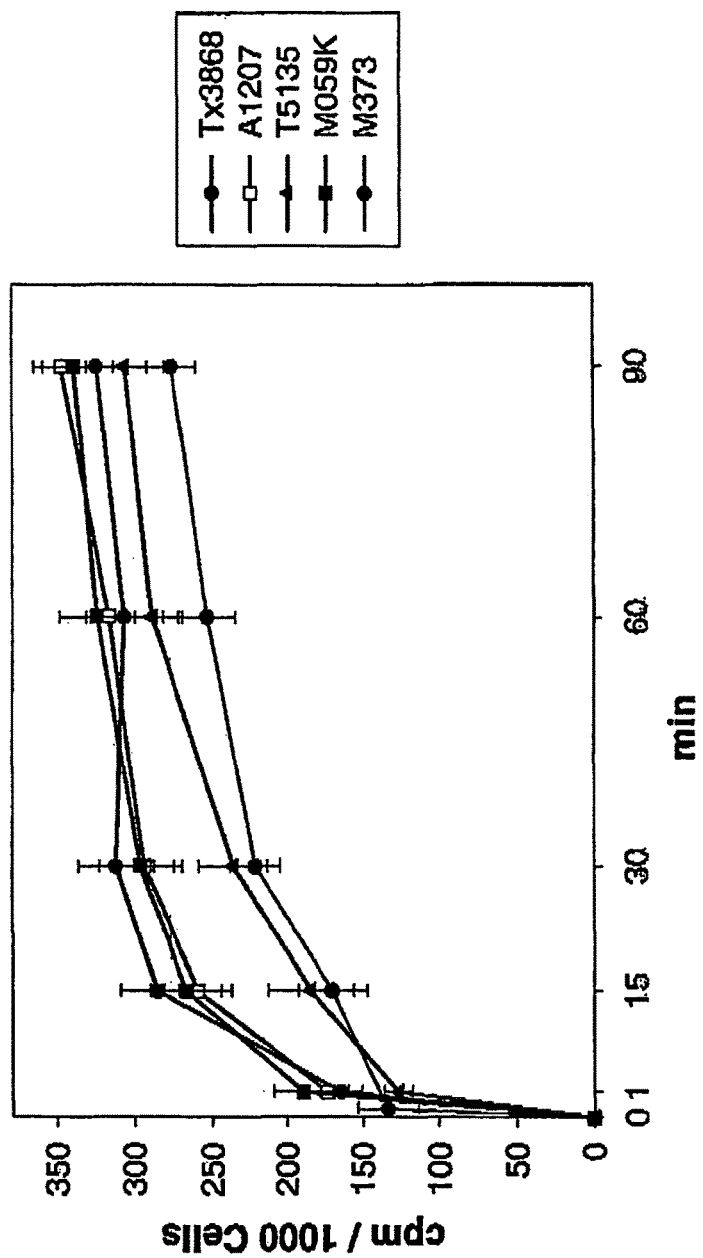

MRI of rats with Cerebral C6-glioma (A) before and (B) after therapy with IPA-131

Tumor targeting of IPA-124 in a patient with glioma

12a

12b

12c

Tumor targeting of IPA-131 in a patient with glioma

Tumor targeting of IPA-123 in a patient with glioblastoma

14a

14b

14c

Whole body distribution of IPA-123 in a patient with oligodendroglioma

THERAPY OF MALIGNANT NEOPLASIAS

RELATED APPLICATIONS

This application claims the benefit of to U.S. provisional application No. 60/738,402, filed Nov. 18, 2005. The contents of this provisional application are incorporated herein by reference.

The present invention provides a method for the treatment of malignant neoplasias comprising the step of administering an L-phenylalanine conjugated to a beta- or alpha-emitting isotope to a subject in the need thereof. Moreover, the invention provides a method for the monitoring of the progress of such treatment of malignant neoplasias.

A variety of documents is cited throughout this specification. The disclosure content of said documents including manufacturer's manuals is herewith incorporated by reference in its entirety.

Malignant gliomas (glioblastomas, astrocytomas, oligodendrogliomas, and ependymomas) are among the least understood and most incurable malignancies. They account for more than 60% of all primary brain tumors, with an annual incidence of 3 to 4 per 100000 population. Gliomas manifest with a peak incidence between 45 and 70 years but may manifest at any age [1, 2]. Despite aggressive treatment, including surgery followed by radiotherapy up to a total dose of 60 Gy, additional brachytherapy or stereotactic radiosurgery and chemotherapy, the overall survival rate of patients with malignant gliomas has remained virtually unchanged for decades: a 5% 2-year survival rate for glioblastomas and less than 20% 10-year survival rate for patients with low-grade astrocytomas have been recorded [1-6]. In order to overcome these dismal prospects, various other experimental therapies have been administered, among them gene therapy with the herpes simplex thymidine kinase gene, methods for sensitising glioma cells to the induction of apoptosis, boron neutron capture, implantation of iodine-125 seeds, locoregional radioimmunotherapy, photodynamic therapy with 5-aminolevulinic acid, or aim at different targets like the coagulation system, to name only some [6-12]. Unfortunately, in spite of all these efforts the prognosis of malignant gliomas remains poor, and no significant improvement in median survival has been demonstrated.

The main pathological problem is the infiltrative nature of these tumors. Even if nearly complete tumor resection is performed, billions of undetectable tumor cells are left belong the resection margins, resulting to recurrences or/and tumor progressions. Moreover, beyond the upper limit of surgery and standard radiation therapy used for these tumors, there is a substantial risk of damaging healthy tissue adjacent to the diseased area. Accordingly, there is a need in the field for a promising therapy approach which is capable to systemically target and eliminate tumor cells which are present in solid tumors, residual tumors and single malignant cells.

Thus, the technical problem underlying the present invention is to provide means and methods for an advanced treatment of malignant neoplasias. The solution to this technical problem is achieved by the embodiments characterized in the claims.

Accordingly, the present invention relates to a method for the treatment of malignant neoplasia, the method comprising the steps of administering a L-phenylalanine conjugated to an alpha-, beta- or Auger-electron emitting isotope selected from the group consisting of bromine-76, bromine-77, bromine-82, iodine-123 (see reference example), iodine-124, iodine-125, iodine-131, and astatine-211 to a subject in the need thereof.

The term "malignant neoplasia" describes in the context of the present invention a cancer, carcinoma, sarcoma, or other tumor, characterised by progressive, uncontrolled, invasive and or metastatic growth. A malignant neoplasia may lead invariably to death if not treated.

An indication to treat a subject with the method of the invention is also the diagnosis of minimal residual disease preferably early solid tumor, advanced solid tumor or metastatic solid tumor, which is characterized by the local and non-local recurrence of the tumor caused by the survival of single cells.

According to the invention it is envisaged that a L-phenylalanine is conjugated to an alpha-, beta- or Auger-electron emitting isotope selected from the group consisting of bromine-76, bromine-77, bromine-82, iodine-124, iodine-125, iodine-131 and astatine-211. Exemplary for the compounds of the invention and in particular as a proof of principle for IPA-131, orphan status was granted by the EMEA on Apr. 11, 2006 under the EU designation number EU/3/061363.

The term "alpha-, beta- or Auger-electron emitting isotope" defines in the context of the present invention radioactive isotopes, characterised by the emission of different particles (rays) formed during radioactive decay or by nuclear transition processes. An alpha emitting isotope is defined as a radioactive nuclide emitting alpha particles, corresponding to a helium nucleus consisting of two protons and two neutrons. A beta emitting isotope is defined as a nuclide emitting fast nuclear electrons (negatrons) formed during radioactive decay. An Auger-electron emitting isotope is defined as a nuclide emitting low energy nuclear electrons, formed by nuclear electron capture or internal transition processes. The maximum path lengths of these particles are in a range from 10 nm to 12 mm. The corresponding L-phenylalanine derivatives are presented in the general formula I:

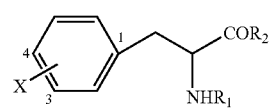

General formula I

In which,

X is bromine-76, bromine-77, bromine-82, iodine-123 (see reference example), iodine-124, iodine-125, iodine-131 or astatine-211 linked to L-phenylalanine at the 3-(meta-) or 4-(para-) position within the aromatic ring.

$R_1$ is H, alkyl group, amino acid, peptide, protein and other biological linker or pro-drug to facilitate or improve tumor targeting.

$R_2$ is OH, amino acid, and other biological structure, which can be use as pro-drug to facilitate or improve tumor targeting.

Preferred conjugates according to the formula I are those in which X is a bromine-77, bromine-82, iodine 124, iodine-125, iodine-131, or astatine-211 linked to L-phenylalanine at the para-position of the aryl group, while $R_1$ is H and $R_2$ is OH.

According to the physical half life of the radionuclide conjugated to the L-phenylalanine, also the conjugates have a corresponding half life of 16.2 h for bromine-76, 57.04 h for bromine-77, 35.3 h for bromine-82, 13.27 h for iodine-123 (see reference example), 4.17 d for iodine-124, 59.41 d for iodine-125, 8.02 d for iodine-131 or 7.21 h astatine-211 labelled L-phenylalanine, respectively. As described in more detail in the appended examples, the halogen isotope may e.g. be conjugated following a protocol for a "non-carrier-added" (n.c.a.) conjugation as well as following a protocol for a "carrier-added" (c.a.) conjugation.

The L-phenylalanine conjugated to an alpha-, beta- or Auger-electron emitting isotope may be administered to the subject in the need thereof via a parenteral, transdermal, intraluminal, intra-arterial, intrathecal or intravenous route or by direct injection into malignant tissue. Also within the scope of the invention is an administration wherein the L-phenylalanine conjugated to an alpha-, beta- or Auger-electron emitting isotope is bound to a matrix of a medically device. The conjugate may be bound for example to a suitable matrix via an amino binding between the amino group of the phenylalanine and a matrix coated with polypeptides. The medical device may be e.g. a wound plating such as a gauze, a metal plating or different, preferably biological, carrier material.

It is preferred that the effective compound is formulated in form of a pharmaceutical composition to the subject in the need thereof.

In accordance with this invention, the term "pharmaceutical composition" relates to a composition for administration to a subject, preferably a human patient. As generally noted above the pharmaceutical composition is preferably administered parenterally, transdermally, intraluminally, intra-arterially, intrathecally or intravenously. Also preferred is a direct injection of the pharmaceutical composition into malignant tissue. It is in particular envisaged that said pharmaceutical composition is administered to a patient via infusion or injection. Administration of the suitable compositions may be effected by different ways, e.g., by intravenous, subcutaneous, intraperitoneal, intramuscular, topical or intradermal administration. The pharmaceutical composition may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preferred dosages for the administration of the L-phenylalanine conjugated to an alpha-, beta- or Auger-electron emitting isotope are described herein below. The compositions may be administered locally or systematically. Administration will generally be parenteral, e.g., intravenous. In an preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition might comprise proteinaceous carriers, like, e.g., serum albumin or immunoglobulin, preferably of human origin. It is envisaged that the pharmaceutical composition might comprise, in addition to L-phenylalanine conjugated to an alpha-, beta- or Auger-electron emitting isotope, further biologically active agents, depending on the intended use of the pharmaceutical composition. Examples for such further biologically active agents are described herein below in the context of concomitant therapy steps of the method of the invention.

Generally, the L-phenylalanine conjugated to an alpha-, beta- or Auger-electron emitting isotope is administered in doses of $10^{-5}$ to $10^{-18}$ g/kg body weight. More preferably, the L-phenylalanine conjugated to an alpha-, beta- or Auger-electron emitting isotope is administered in doses of $10^{-8}$ to $10^{-10}$ g/kg body weight. It is preferred that such dose is formulated contained in 1 to 10, preferably 2 to 5 ml of sterile solution, such as phosphate buffered saline solutions, water for injection, etc.

It has been surprisingly found that the above described conjugates are capable to accumulate specifically in low and high grade gliomas as well as other malignant cells/tissues which can be subsumed under the above provided definition of malignant neoplasia. Furthermore, it has been found that the conjugates are capable to cross the blood-brain barrier which is an essential feature for a treatment of a malignant neoplasia which is located behind said blood-brain barrier. Due to the specific accumulation of the L-phenylalanine conjugated to an alpha-, beta- or Auger-electron emitting isotope this conjugate is useful in a method for the treatment of such malignant neoplasia by specifically targeting the malignant cells and tissue and to destroy it by the irradiation activity of the emitting isotope.

The effectiveness and safety of single photon emission tomography (SPET) with 4-[$^{123}$I]iodo-L-phenylalanine (IPA-123) for brain tumour imaging not only in the experimental C6 glioma model but also in patients with malignant gliomas has been demonstrated by the inventor [13, 14]. This data demonstrates that IPA-123 (see reference example) in fact crosses the blood-brain barrier after intravenous administration and accumulates specifically in low and high grade gliomas with surprisingly marked retention in tumor cells [14]. Moreover, and advantageous for the safety of the method of the invention, it was demonstrated that the accumulation in the normal cerebral parenchyma is moderate and decreases rapidly with time. Human studies using 4-[$^{124}$I]iodo-L-phenylalanine (IPA-124), and 4-[$^{131}$I]iodo-L-phenylalanine (IPA-131) have shown additionally that tumor targeting and retention in glioma tissue in human patients is comparable for the tested embodiments of the invention, independently of the radionuclide chosen.

In addition to the therapeutic beta-emission, IPA-124 also displays a strong positron emission allowing for positron emission tomography (PET) imaging. Furthermore, IPA-124 possesses a long half life of 4.2 days. Using IPA-124, it was demonstrated in accordance with the present invention that IPA-124 is retained by gliomas in high concentrations for at least 6 days after administration, thus evidencing the potential to apply a sustained continuous therapeutic internal radiation dose.

Moreover, serial IPA-124 PET imaging showed that surgical resection, when planned solely based on conventional structural magnetic resonance imaging (MRI) and computed tomography (CT), grossly underestimates the true extent of tumor disease requiring therapy, as shown by the extensive IPA-124 signal remaining around the resection margins postoperatively.

It is preferred, that the malignant neoplasia is selected from a group consisting of malignant glioma, prostatic and breast cancer. More preferably, the glioma is selected from the group consisting of glioblastoma multiforme, anaplastic astrozytome, astrooligodendroglioma and oligoastrozytoma.

As described herein above it is preferred that the conjugated L-phenylalanine is administered intravenously. The intravenous administration may be effected by administering the conjugate in form of an above described pharmaceutical composition for parenteral administration.

It is also preferred that the irradiation dose of the alpha-, beta or Auger-electron emitting isotope conjugated to the L-phenylalanine is in the range of 0.1 to 1000 MBq/kg body weight. Generally, but not exclusively, this dose range overlaps with the above indicated dose range, calculated in terms of g/kg body weight. More preferably, the irradiation dose of the alpha-, beta- or Auger-electron emitting isotope is in the range of 10 to 400 MBq/kg body weight. The administered dose is determined using an appropriate dose meter, calibrated to quantitatively measure alpha, beta or gamma radiation.

It is also preferred that the irradiation dose of the alpha-, beta- or Auger-electron emitting isotope conjugated to the L-phenylalanine is administered as a single dose once or as a fractionated dose in 2 to 60 fraction doses. More preferably, the conjugate is administered fractionized in 2 to 10 fraction doses. Dose fractionation is an established procedure in radiation therapy. By fractionating a total administered dose, improved tolerability for healthy non-target tissue, as well as an increased cytotoxic effect to tumor tissue is achieved. Repeated fractionated irradiation allows to therapeutically impact a higher percentage of cells in radiation sensitive stages of the cell cycle, compared to a one time single high dose irradiation. Therapeutic irradiation induces single and double strand breaks of DNA, which is counteracted by nuclear repair mechanisms upregulated following irradiation. It is believed, that cells undergoing DNA repair, are more susceptible to a renewed irradiation than radiation-naïve cells.

In a further preferred embodiment of the method of the invention the conjugated L-phenylalanine is 4-[131I]iodo-L-phenylalanine (IPA-131), 4-[$^{124}$I]iodo-L-phenylalanine (IPA-124) or 4-[$^{211}$At]astatine-L-phenylalanine. Iodine-131 is widely available, has a favourable half life and can be handled by most institutions licensed to apply open radionuclides. Iodine-131 allows for convenient extracorporal therapy monitoring using a gamma camera owing to a gamma ray component, emitted in a fixed ratio relative to the therapeutic beta particle emission, which is itself not detectable extracoprorally.

Another preferred embodiment of the method of the invention makes use of 4-[$^{124}$I]iodo-L-phenylalanine. Iodine-124 has a positron emission component, allowing for PET imaging, in addition to the therapeutic beta-emission. Using quantitative PET imaging, internal dosimetry measurements or an ongoing basis can be conducted for therapy planning and therapy monitoring for a period of up to 15 days following a single injection. Astatine-211 is also preferred, as it emits high energy (6.8 MeV) alpha particles, with a short path length in tissue (65 µm), allowing administration of a highly cytotoxic radiation to targeted tissue, while minimising undesirable radiation effects to non-target tissue.

In an also preferred embodiment of the invention it is envisaged that the method further comprises the step of a treatment of the subject by a concomitant therapy. Said concomitant therapy may be selected from the group consisting of a surgical therapy, a chemotherapy, a radiotherapy, an immunotherapy, a gene therapy, a vaccine therapy, an antisense nucleotide therapy, an siRNA therapy, an intracavitary therapy, or a device-based treatment. The step of the concomitant therapy may be effected prior, simultaneous or subsequent to the step of administering a L-phenylalanine conjugated to an alpha-, beta- or Auger-electron emitting isotope.

Methods and means for concomitant therapies are well known in the art. An example for a surgical therapy may comprise a resection of a solid tumour or of malignant tissue. An example for a chemotherapy may comprise the administration of an bioactive agent known to be effective in retarding or arresting the malignant growth or to be effective in the regression or deletion of malignant tissues or cells. Such agents might be e.g. drugs acting as cytostatics. Accordingly, a chemotherapy comprises in line with the medical standards in any systemic or local treatment the administration of cytostatic or cytotoxic agents. Chemotherapeutic agents used in oncology include among others, nitroso urea compunds (ACNU [nimustin], BCNU [carmustin], CCNU [lomustin]), temozolomid, procarbacin, metothrexate, cytarabin, gemcitabine, fluorouracil, cyclophosphamide, mitoxantron, anthracyclins, estramustin, or taxanes. The chemotherapeutic agents are administered in appropriate dosing regimens according to medical practise. In line with the invention nitroso urea compunds, temozolomide, procarbacin, and methotrexate are preferred chemotherpeutic agents.

A radiotherapy is known in the art as a therapy comprising the application of an external irradiation dose to a patient.

Examples for immunotherapy comprise but are not limited to the administration of compounds such as antibodies, antibody fragments and/or derivatives thereof which specifically detect malignant tissue or cells and/or cell with the ability to eliminate the malignant tissue or cells. The specific detection of malignant tissue or cells may be effected via the detection of tumor specific markers by the antibodies, antibody fragments and/or derivatives thereof. A tumor-specific marker is a tumor-associated cell surface antigen which is either found exclusively on tumor cells or is overexpressed on tumor cells as compared to non-malignant cells. Tumor-associated cell surface antigens can be expressed not only on tumor cells but also on cells/tissue which are/is not essential for survival or which can be replenished by stem cells not expressing tumor-associated cell surface antigen. Furthermore, tumor-associated cell surface antigen can be expressed on malignant cells and non-malignant cells but is better accessible by a therapeutic agent of interest on malignant cells. Examples of over-expressed tumor-associated cell surface antigens are Her2/neu, EGF-Receptor, Her-3 and Her-4. An example of a tumor-associated cell surface antigen which is tumor specific is EGFRV-III. An example of a tumor-associated cell surface antigen which is presented on a cell which is non-essential for survival is PSMA. Examples of tumor-associated cell surface antigens which are presented on cells which are replenished are CD19, CD20 and CD33. An example of a tumor-associated cell surface antigen which is better accessible in a malignant state than in a non-malignant state is EpCAM. Moreover, an immunotherapy may comprise the administration of agents such as T-cell co-stimulatory molecules or cytokines, agents activating B-cells, NK-cells or other cells of the immune system as well as drugs inhibiting immune reactions (e.g. corticosteroids).

The term "gene therapy" defines in the context of the invention a therapy comprising the administration of one or more nucleic acid constructs functionally encoding e.g. one or more antigens which are characteristic for malignant cells. Such antigens comprise tumor specific markers. The sequence encoding such antigen is operably linked to a nucleic acid sequence which is a regulatory sequence. Thus, a gene therapy comprises the functional expression of a heterologous gene in a patient according to standard medical protocols using appropriate vector systems known in the art; see e.g. Haberkorn et al., Curr Med Chem. 2005; 12(7):779-94. The term "regulatory sequence" refers to DNA sequences which are necessary to effect the expression of coding sequences to which they are ligated. Control sequences in the context of the described gene therapy generally include promoters, terminators and, in some instances, enhancers, transactivators or transcription factors. The term "control sequence" is intended to include, at a minimum, all components the presence of which are necessary for expression, and may also include additional advantageous components. The term "operably linked" refers to a arrangement/configuration wherein the components so described are in a relationship permitting them to function in their intended manner. A control sequence "operably linked" to a coding sequence is ligated in such a way that expression of the coding sequence is achieved under conditions compatible with the control sequences.

A vaccine therapy is in the context of the present invention a therapy aiming at activating the innate or adaptive immune system of the patient to act against the tumor tissue or the malignant cells. Such therapy comprises e.g. administering one or more antigen preparations containing tumor substances, or cells selected to react against tumor tissue or the malignant cells.

An antisense therapy is a therapy e.g. using nucleotide sequences being complementary to tumor-specific gene sequences, aiming at functionally neutralising tumor gene expression, and consequently inducing tumor cell death.

An siRNA therapy is a therapy using small interfering RNAs capable of sequence-specifically silencing the expression and activity of various tumor-specific target genes by cleaving specific unique sequences in the mRNA transcript of the target gene and disrupting translation of the target mRNA, consequently inducing tumor cell death.

A concomitant therapy which requires the administration of additional bioactive agents which are effective in the treatment of the malignant neoplasia may be accompanied by the administration of additional compounds which minimize potential side effects of said bioactive agents such as drugs acting on the gastro-intestinal system, drugs preventing hyperuricemia, and/or drugs acting on the circulatory system, e.g. on the blood pressure, known in the art.

In a preferred embodiment of the method of the invention the concomitant therapy is a percutaneous radiotherapy. Percutaneous radiotherapy is typically administered as external beam radiation stemming from among others, radioactive cobalt-60 sources, linear accelerators, proton, neutron, or hadron beam sources. Preferably, the irradiation is started in a period of 0 to 7 days subsequent to the administration of the conjugated L-phenylalanine. More preferably, the irradiation is started in a period of 0.5 to 24 hours subsequent to the administration of the conjugated L-phenylalanine.

The above described concomitant radiotherapy may comprise a cumulative external irradiation of a patient in a dose of 1 to 100 Gy. A preferred range of the irradiation dose is 1 to 60 Gy. It is preferred that the external irradiation dose is administered in 1 to 60 fractional doses, more preferably in 5 to 30 fractional doses. Preferably, the fractionized doses are administered over a period of 1 to 26 weeks, more preferably over a period of 6 to 12 weeks. In accordance with the present invention, the term 'fractional dose' is to be understood to mean that the overall activity of the fractional dose adds up or essentially adds up to the cummulative external irradiation otherwise also achievable by administering one single dose.

It is preferred that the subject to be treated by the method of the invention is a human subject.

In an alternative embodiment the invention relates to a method for the monitoring of the progress of a treatment of malignant neoplasia, the method comprising the steps:

(a) administering a L-phenylalanine conjugated to an alpha-, beta- or Auger-electron emitting isotope selected from the group consisting of bromine-76, bromine-77, bromine-82, iodine-123 (see reference example), iodine-124, iodine-125, iodine-131 and astatine-211 to a subject in the need thereof; and (b) localizing and/or dosimetrically measuring the conjugated L-phenylalanine in the subject by using a γ-camera. This may be followed by a further step: c) determining the absolute and cumulative activity concentration per volume of exposed tissue, for example at different time points, and calculating the biologically effective dose based thereon, taking into account the biological impact of each radioisotope defined by its physical characteristic. Characteristics include energy and branch ratio of the particles arising from the different types of radioactive decay such as electron emission, alpha-particle emission or Auger-electron emission. An example is given in Example 13 using PET imaging.

A method for the administration of a L-phenylalanine conjugated to an alpha-, beta- or Auger-electron emitting isotope is described herein above. An example for the localization and/or dosimetric measurement of conjugated L-phenylalanine in the subject by using a γ-camera is exemplified in the appended example 10. Human examples of tumor localisation with IPA-124 using PET imaging and with IPA-131 and IPA-123 using SPECT imaging are given in examples 13, 14, and a reference example. Further examples of dosimetry measurements, as determined by SPECT imaging in human glioma patients are given in example 15 for IPA-131 and in a reference example for IPA-123.

The method for the monitoring of the progress of a treatment of malignant neoplasia may also comprise the step of a treatment of the subject by an above described concomitant therapy. As described herein above, the step of the concomitant therapy may be effected prior, simultaneous or subsequent to the step of administering a L-phenylalanine conjugated to an alpha-, beta- or Auger-electron emitting isotope.

Preferably, the conjugated L-phenylalanine is localized and/or dosimetrically measured at least 0 to 7 days, more preferably 0.5 to 48 h subsequent to its administration.

The figures show:

FIG. 1:
Uptake kinetics of IPA-123 in five human glioblastoma cells in vitro

Figure 2:
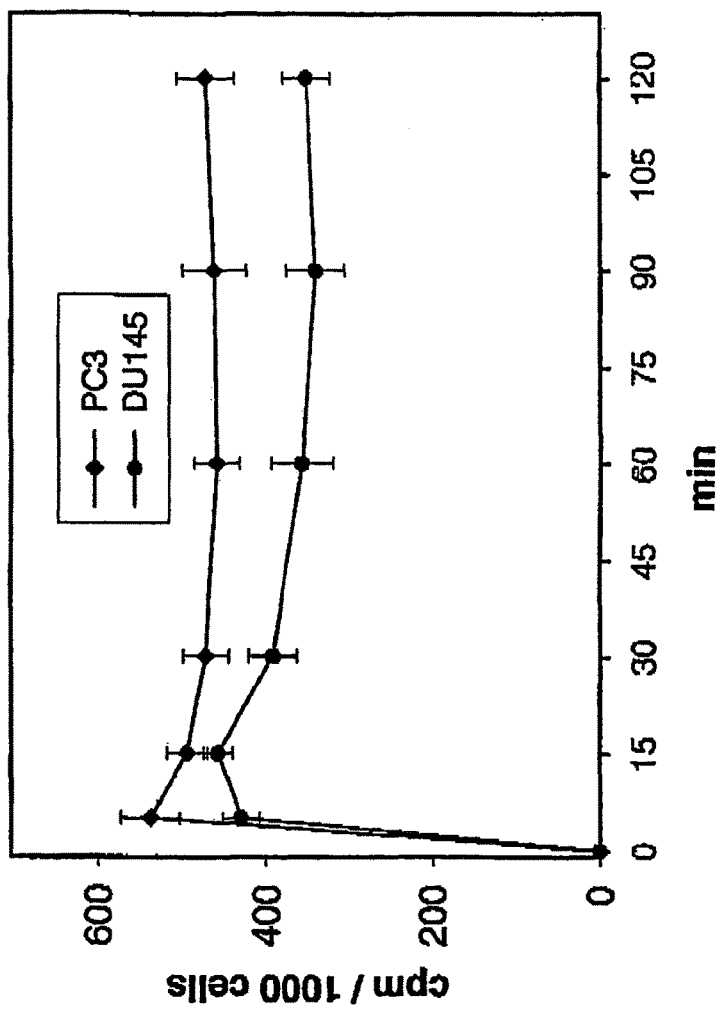

FIG. 2:
Uptake kinetics of IPA-123 in human PC3 and DU425 prostate cancer cells in vitro FIG. 3:
(left) Radioactive dose dependent tumoricidic potential of IPA-131in human A 1207 glioblastoma cells in vitro, (middle, right) Cytocidal effect of IPA-131 on human Tx3868 glioblastoma cells in vitro FIG. 4:
Induction of primary necrosis and apoptosis by IPA-131 vs. external irradiation (15 Gy)

Figure 5:
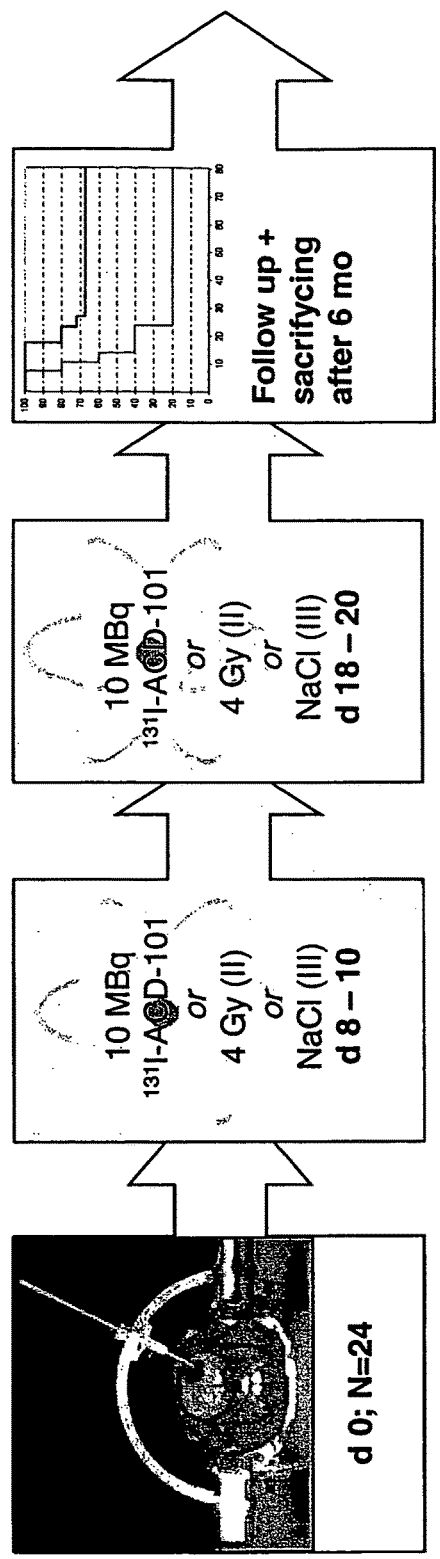
Figure 6:
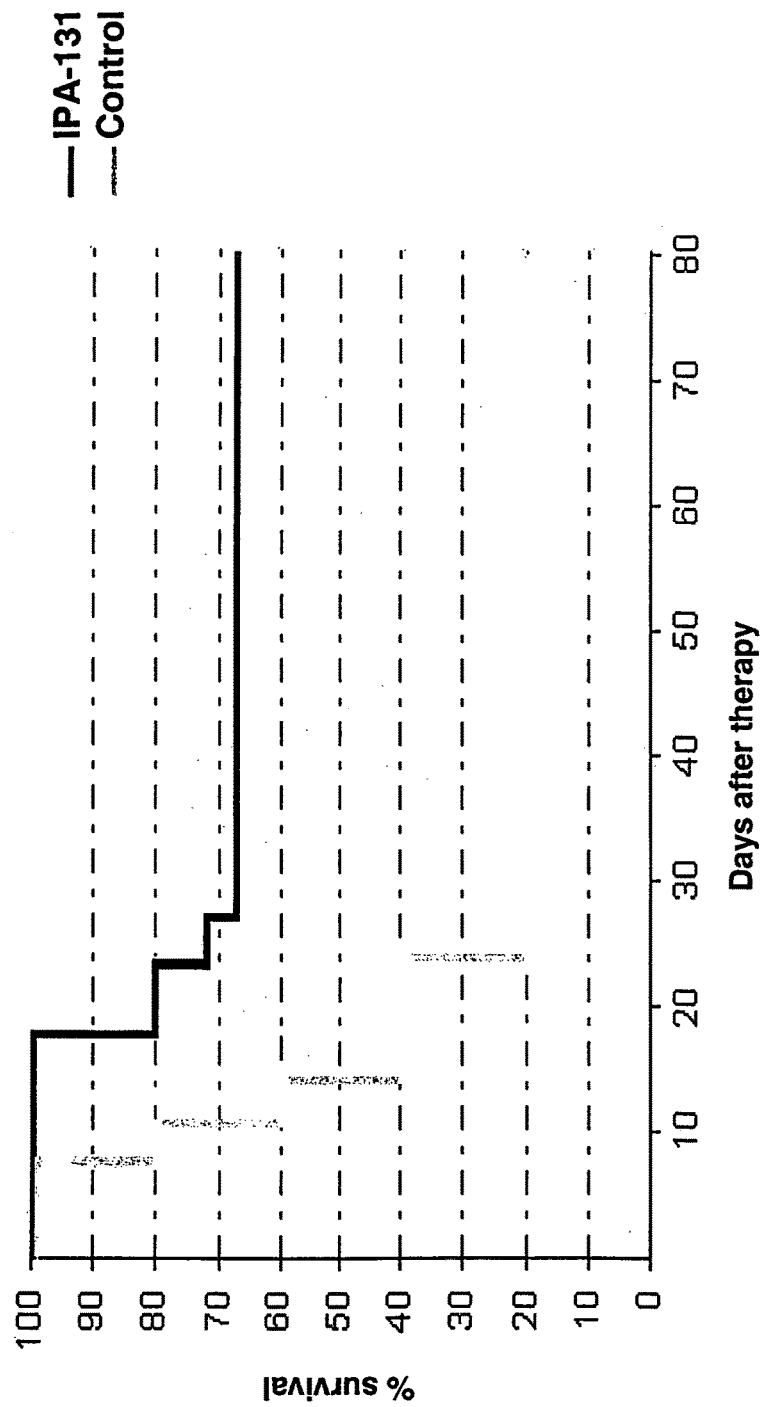

FIG. 5:
Tumoricidal effect of IPA-131 endoradiotherapy on experimental glioblastomas, established orthotopically in the RNU rat model in vivo: experimental design FIG. 6:
Tumoricidal effect of IPA-131 endoradiotherapy (dose 20 MBq) on orthotopically established experimental C6 rat gliomas in RNU rats: Kaplan-Meyer survival curves FIG. 7:
Tumoricidal effect of IPA-131 endoradiotherapy (dose 20 MBq) and maximum tolerable external field radiation therapy (4 Gy) on orthotopically established experimental human Tx3868 glioblastomas in RNU rats: Kaplan-Meyer survival curves FIG. 8:
Tumoricidal effect of IPA-131 endoradiotherapy (dose 20 MBq) and maximum tolerable external field radiation therapy (4 Gy) on orthotopically established experimental human A1207 glioblastomas in RNU rats: Kaplan-Meyer survival curves FIG. 9:
Tumoricidal effect of IPA-131 endoradiotherapy (dose 20 MBq) on orthotopically established experimental C6 rat gliomas in RNU rats: Demonstration of subgaleal and intracerebral tumor disappearance using intravital small animal MRI imaging FIG. 10:
Tumoricidal effect of IPA-131 endoradiotherapy (dose 20 MBq) on orthotopically established experimental human Tx3868 glioblastomas in RNU rats: Demonstration of metabolic normalisation, and histological tumor disappearance using metabolic and H & E staning in fresh-frozen tissue sections FIG. 11:
Tumoricidal effect of IPA-131 endoradiotherapy (dose 20 MBq) on orthotopically established experimental human A1207 glioblastomas in RNU rats: Demonstration of metabolic normalisation, and histological tumor disappearance using metabolic and H & E staining in fresh-frozen tissue sections FIG. 12:
Tumor targeting of IPA-124 in a patient with glioma. Structural MRI images (left). Anatomically corresponding IPA-124 PET images (right) 40-80 min (FIG. 12a) and 6 days (FIG. 12b) post injection of 50 MBq IPA-124. The patient underwent surgically complete tumor resection on day 2: Demonstration of tracer uptake in projection to MRI lesions, and retention of the tracer for at least 6 days. Demonstration of continued IPA-124 activity in resection margins of tumor, indicating subtotal surgical removal. FIG. 12c shows semiquantification of IPA-124 activity in postoperatively remaining tumor tissue using contralateral healthy tissue as a reference region, projected to the pre-operative MRI images as anatomic reference. Tumor activity exceeds reference region activity by a factor of 8.86.

FIG. 13:
Tumor targeting of IPA-131 in a patient with glioma. IPA-131 SPECT images 30 min (FIG. 13a) and 26 h (FIG. 13b) post injection of 100 MBq IPA-131: Demonstration of tumor uptake, and retention for at least 26 hours. FIGS. 13c and 13d show planar whole body images 5 min (FIG. 13c) and 26 h (FIG. 13d) post injection of 100 MBq IPA-131: Determination of organ dosimetry.

Figure 14:
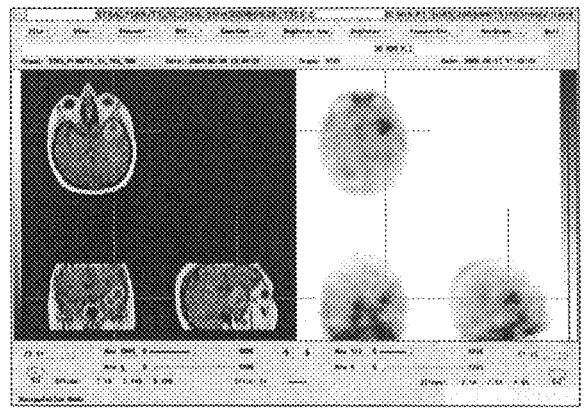
Figure 14:
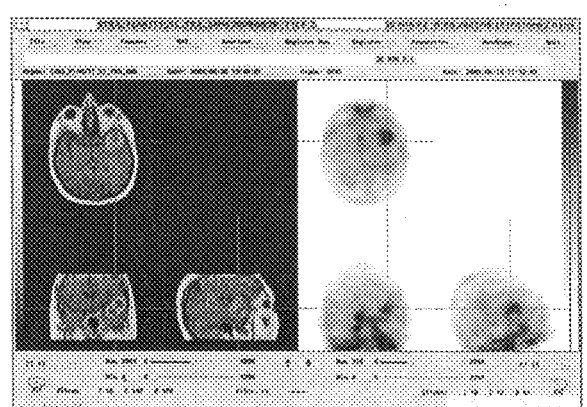
Figure 14:
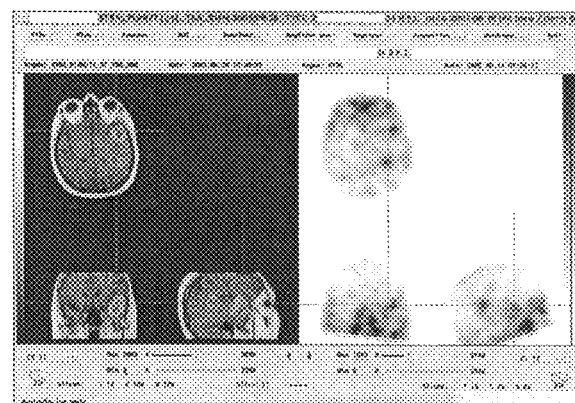

FIG. 14:
Tumor targeting of IPA-123 in a patient with glioblastoma. Structural MRI images (left). Anatomically corresponding IPA-123 SPECT images (right), 30 min (FIG. 14a), 3 h (FIG. 14b), and 24 h (FIG. 14c) post injection of 250 MBq IPA-123: Demonstration of tracer uptake in projection to MRI lesions, and retention of the tracer for at least 24 h.

Figure 15:
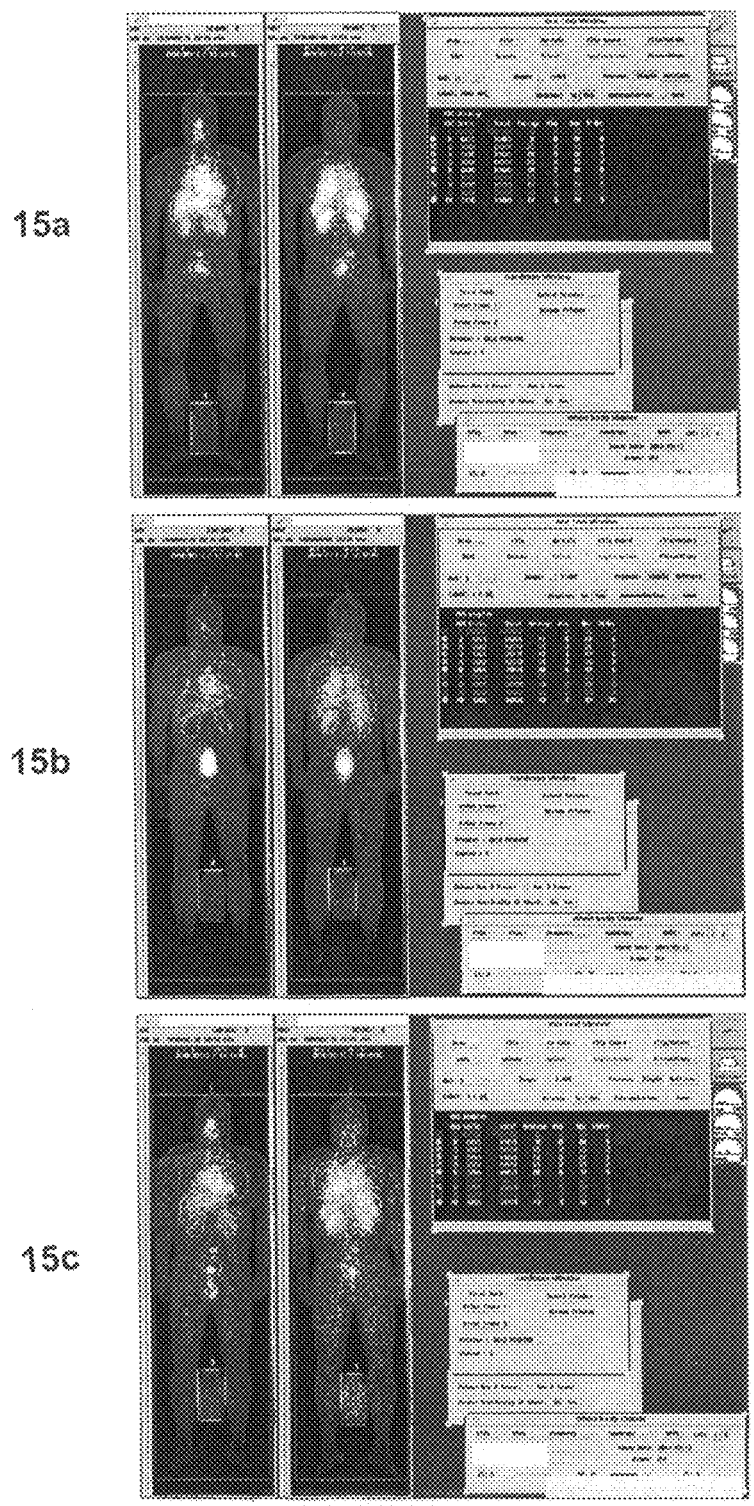

FIG. 15:
Whole body distribution of IPA-123 in a patient with oligodendroglioma. IPA-123 planar whole body images 0 min (FIG. 15a), 1 h (FIG. 15b), and 3 h (FIG. 15c), post injection of 250 MBq IPA-123: Determination of organ dosimetry The invention will now be described by reference to the following examples which are merely illustrative and are not to be construed as a limitation of scope of the present invention.

EXAMPLE 1

4-Bromo-L-phenylalanine (4-BrPA), 3-bromo-L-phenylalanine (3-BrPA), 4-iodo-L-phenylalanine (4-IPA), 4-ter.butyltinn-L-phenylalanine (4-TBSnPA), 3-ter.butyltinn-L-phenylalanine (3-TBSnPA), 4-methylsilyl-L-phenylalanine (4-Me$_3$SiPA) and 3-methylsilyl-L-phenylalanine (3-Me$_3$SiPA) used as starting materials (precursor) for radiolabeling were either purchased commercially or prior synthesized in analogy to the literature. Unless stated otherwise, all other chemicals and solvent were of analytical grade and obtained commercially or via our local hospital pharmacy. Sodium [$^{124}$I]iodide, sodium [$^{125}$I]iodide, sodium [131I]iodide, sodium [$^{77}$Br]bromide, sodium [$^{82}$Br]bromide, and sodium [$^{211}$At]astatine for radiolabeling was obtained in the highest obtainable radiochemical purity, generally in 0.01 N NaOH or in phosphate buffered saline (PBS) from different suppliers. HPLC purification was performed on a Hewlett Packard HPLC system consisting of a binary gradient pump (HP 1100), a Valco 6-port valve with 2500 µl loop, a variable wavelength detector (HP 1100) with a UV detection at 254 nm and a sodium iodide scintillation detector (Berthold, Wildbad, Germany), using reversed-phased column (250×4 mm, Nucleosil-100). The column was eluted at different flow rates in with water/ethanol/acetic acid (89:10:1; v/v) or PBS/ethanol (90:10; v/v).

The proposed radiolabeled phenylalanines were obtained either by non-isotopic halogen exchange (carrier-added/c.a.) or by radio-demetalation of the corresponding precursor as described in the general scheme 1, resulting to no-carrier-added (n. c. a) products after HPLC separation.

Scheme 1: scheme of the radiosyntheses of n.c.a. IPA-124, IPA-125, IPA-131, BrPA-77, BrPA-82 and AtPA-211

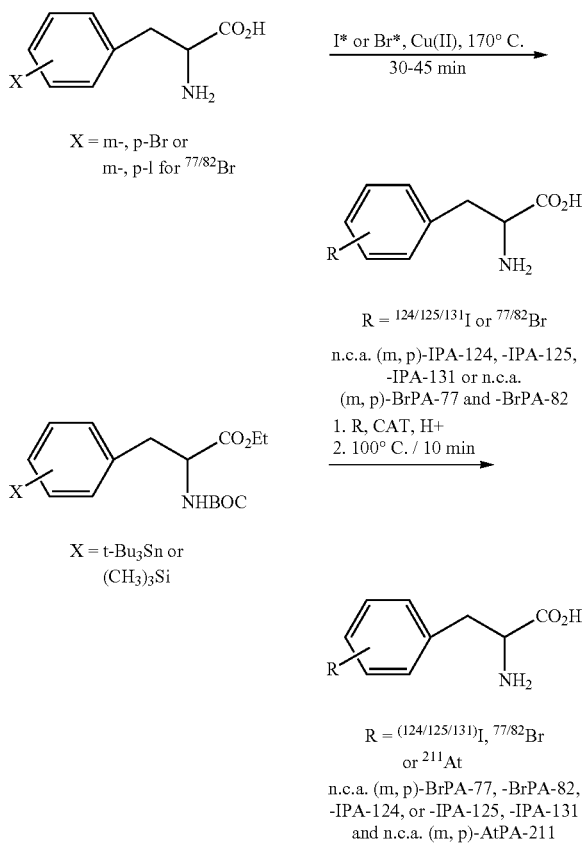

EXAMPLE 2

General synthesis of 3,4-[$^{124}$I]iodo-L-phenylalanine (m, p-IPA-124), 3,4-[$^{125}$I]iodo-L-phenylalanine (m,p-IPA-125) and 3,4-[$^{131}$I]iodo-L-phenylalanine (m,p-IPA-131) by non-isotopic radioiodo-debromination A solution of carrier free sodium [$^{124}$I]iodide, sodium [$^{125}$I]iodide or sodium [$^{131}$I]iodide (up to 5 GBq) and 5 µl aqueous $Na_2S_2O_5$ (4.0 mg $Na_2S_2O_5$/ml) was evaporated to dryness by passing a stream of nitrogen through a reaction vessel at 100° C., followed by addition of 200 µl of the corresponding L-bromophenylalanine (0.25-0.5 mg/ml 0.1 N $H_3PO_4$), 20 µl aqueous L-ascorbic acid (10 mg/ml) and 20 µl aqueous Cu(II) sulphate (0.10 mol/l). The reaction vessel was heated for 30 min at 170° C., cooled and the mixture diluted with up to 500 µl water. The radioiodinated product was separated from unreacted starting materials and radioactive impurities by HPLC.

Generally, 3/4-IPA-124, 3/4-IPA-125 and m/p-IPA-131 were obtained in 88±10% radiochemical yield, with a specific activity >500 GBq/µmol. The fraction containing the radioiodinated products was collected into a sterile tube, buffered with 0.5 M phosphate buffered saline (pH 7.0; Braun, Melsungen, Germany), and sterile filtered through a 0.22 µm sterile membrane (Millex GS, Millipore, Molsheim, France) to an isotonic and injectable radiopharmaceutical for in vitro and in vivo investigations.

EXAMPLE 3

Synthesis of 3,4-[$^{124}$I]iodo-L-phenylalanine (m, p-IPA-124), 3,4-[$^{125}$I]iodo-L-phenylalanine (m,p-IPA-125), 3,4-[$^{131}$I]iodo-L-phenylalanine (m,p-IPA-131)), and 3,4-[$^{211}$I]astatine-L-phenylalanine (m, D-AtPA-211) by iodo-demetalation Alternatively (m, p)-IPA-124, (m, p)-IPA-125, (m, p)-IPA-131, and (m, p)-AtPA-211 were prepared by iodo-demetalation in acidic condition in the presence of chloramine-T for in situ oxidation of the corresponding radioiodide and astatine-211, using the protected tributyltin- or trialkylsilyl-L-phenylalanine as starting material. In details: Sodium [$^{124/125/131}$I]iodide (up to 2 GBq in 50 µl PBS) was added to a mixture consisting of protected (m,p)-tert. tributyltin- or trialkylsilyl-L-phenylalanine (50-80 µg) in 50 µl of methanol and 10 µl of 1 N HCl in a 1 ml-vial, followed by 5 µl aqueous chloramine-T (CAT) from a solution of 1 mg CAT/ml water, while shaking. After a 2 min reaction time at room temperature, 20 µl aqueous $Na_2S_2O_5$ (4.0 mg $Na_2S_2O_5$/ml) was added to the reaction vessel to bind the unreacted free radioisotope, followed by deprotection of the amino and carbonyl groups under acidic condition at 100° C. (m, p)-IPA-124, (m, p)-IPA-125, (m, p)-IPA-131, and (m, p)-AtPA-211 were isolated by HPLC and formulated as described above for in vitro and in vivo studies. The radiochemical yields were >90%, with a specific activity >1000 GBq/pmol.

EXAMPLE 4

Synthesis of 3,4-[$^{82}$Br]bromo-L-phenylalanine (m, p-BrPA-82) and 3,4-[$^{77}$Br]bromo-L-Phenylalanine (m,p-BrPA-77)

(m, p)-BrPA-82 and (m, p)-BrPA-77 were prepared either by non-isotopic [$^{77/82}$Br]bromo-deiodination at 160° C. or by [$^{77/82}$Br]bromo-demetalation, using (m,p)-iodo-L-phenylalanine or the corresponding (m,p)-tributyltin- or (m, p)-trialkylsilyl-L-phenylalanine, as starting materials in analogy to the procedure described above. (m, p)-BrPA-82 and (m, p)-BrPA-77 were isolated by means of HPLC as no carrier-added products with a specific activity >500 GBq/µmol. The fractions containing the radiobrominated products were buffered with phosphate buffered saline (PBS), and sterile filtered through a 0.22 µm sterile membrane to an isotonic and injectable radiopharmaceuticals for in vitro and in vivo investigations.

EXAMPLE 5

Cell Lines and Cell Cultures

Five human glioma cell lines, one rat glioma cell line, two human prostate cancer cell lines and one human breast cancer cell line were investigated. The human glioma cell lines Tx 3868 and T 5135 (from primary human glioblastoma multiforme), and the rat C6 glioma cells were provided by the Institute of Human Genetics, University of the Saarland (Homburg, Germany). The human high-grade glioma cells, designated as A1207, M059K and U373MG, the human prostate cancer cell lines PC3 and DU425, and the human breast cancer cell line MCF-07 (American Type Culture Collection, Rockville, Md.), were purchased commercially or provided by the oncological research laboratory of the University Medical Center of Saarland (Homburg, Germany). Cells were cultivated in RPMI-1640 medium or in Dulbecco's modified Eagle medium (sodium pyruvate-free, supplemented with L-glucose and pyridoxine), respectively, supplemented with 10% (v/v) heat-inactivated foetal calf serum (FCS), penicillin (50 U/ml), streptomycin (50 µg/ml), and 50 µl insulin (PromoCell, Heidelberg, Germany). All cells lines were maintained in appropriate flasks in a humidified incubator (5% $CO_2$) at 37° C. Before the experiment, subconfluent cell cultures were trypsinized with a solution of 0.05% trypsin containing 0.02% EDTA but without $Ca^{2+}$ and $Mg^{2+}$, and resuspended in fresh medium to various cell concentrations after counting by vital staining on a hemocytometer, depending upon the study. Cells were free of mycoplasms. Viability of the cells was >95%.

EXAMPLE 6

Internalisation Experiments

Uptake experiments were undertaken to evaluate the affinity of the proposed L-phenylalanine derivatives for the proposed human tumors, and to assess their therapeutic activity in vitro.

All experiments were performed fourfold, simultaneously with 250000, 500000 and $10^6$ freshly prepared human tumor cells, including human malignant glioma, prostatic and breast cancer cells. Before experiments, subconfluent cells were trypsinized as described above. The suspension was mixed thoroughly, transferred to a 50-ml centrifuge tube (Falcon®, Becton Dickinson, USA). Cells were centrifuged for 5 min at 200×g; the resulting supernatant was removed and the pellet resuspended in serum-free Dulbecco's Mod Eagle medium and then transferred to Eppendorf tubes at concentrations of $10^6$ cells/ml for the uptake investigations.

Before incubation with the corresponding radiolabeled phenylalanine, the tumor cells were preincubated for 5 min in 500 µL medium at 37° C. in 1.5-ml Eppendorf centrifuge tubes. Aliquots of 30-50 µL ($10^6$-1.5×$10^6$ cpm) freshly prepared radiopharmaceutical were added and cells incubated at 37° C./5% $CO_2$ for 1, 2, 5, 15, 30, 60, 90 and 120 min while shaking. Uptake was stopped with 500 µL ice-cold PBS (pH 7.4) and an additional 3-min in an ice bath, the cells were centrifuged for 2 min at 300×g, the supernatant removed and the pellet washed three time with ice-cold PBS. Cell pellets were counted for radioactivity together with 3 aliquots of standards on a Berthold LB951 counter. The percentage of binding of the radiopharmaceutical was calculated by the formula: (cpm cell pellet/mean cpm radioactive standards)×100. The results were expressed either as percent of the applied dose per $10^6$ cells or as cpm/1000 cells for better comparison.

EXAMPLE 7

Evaluation of the Cell Survival Rate After Treatment with Radiolabeled L-Phenylalanines After development of a confluent lawn of cells, the cultures were exposed to 0.001-10 µCi/ml of the corresponding radiopharmaceutical for up to 48 hours at 37° C./5% $CO_2$. In a parallel experiment, cells were irradiated using a 6-MeV linear accelerator with doses from 2 to 15 Gy for comparison of cell survival rate of both methods. In order to be able to observe the morphology of the glioma cells, the cells were grown on standard glass slides or in standard culture dishes. Then the medium was removed and the cells were fixed either in 70% ethanol for at least 30 min on ice for flow-cytometric analyses after staining or in 4% neutral buffered formalin for immunohistopathological analyse.

EXAMPLE 8

Tumor Models

All animal experiments were conducted in accordance with the Guide for the Care and Use of Laboratory Animals published by the US National Institutes of Health (NIH Publication No. 85-23, revised 1996) and in compliance with the German animal protection law. Experiments were approved by the local district government (Saarpfalz-Kreis, AZ: K 110/180-07, 02/99-02/04).

The first studies were carried out on in male Wistar rats for C6 rat glioma model and in RNU rats for human glioma models. Wistar rats and RNU rats were from Charles River (Sulzfeld, Germany). The C6 rat glioma model has been previously described in detail [13, 18]. Its biological behavior closely simulates that of human high-grade gliomas.

One million ($10^6$) C6 rat glioma cells or $10^6$ primary human Tx3868, T5131, A1207, M059K and U373MG high-grade glioma cells were stereotactically implanted into the left frontal region of Wistar rats or RNU rats while under chloral hydrate anaesthesia as described previously [13, 18]. The animals were held in metabolic cages. Previous histopathological metabolic investigations showed that after intracerebral implantation the models form a progressively growing, infiltrative tumor with islands of malignant cells at varying distances from the centrally growing mass. For each cell line, 6 animals with radiologically (MRI or by gamma camera) confirmed brain tumor were randomly chosen as control animals, a second group of 15 animals were treated with 20 MBq of the radiolabeled L-phenylalanine in two fractions of 10 MBq each via a Teflon catheter in a tail vein 9 and 18 days after tumour implantation. While a third group of 15 rats were irradiated with 4-8 Gy. Survival time was calculated according to the Kaplan-Meier method. Surviving animals were sacrificed after 90 and 180 days. All rat brains were examined histologically after biopsy.

The second investigation was conducted in SCID mice bearing human prostate or breast cancer to assess the uptake characteristics and the tumor affinity of the radiolabeled L-phenylalanines after intravenous injection and to evaluate their therapeutic potential. Tumor cells (2.5-5×$10^6$ cells in 100 µl PBS) were inoculated into the flank of the animals. After tumor implantation, the animals were inspected daily for complications and checked for tumor formation visually and by palpation. Tumor size was calculated by the following formula: tumor volume ($cm^3$)=$W^2$×L×½; where L is the length (cm) and W the width (cm) of the tumor. Tumor growth was additionally monitored non-invasively by magnetic resonance imaging, starting 10 days after implantation.

EXAMPLE 9

Magnetic Resonance Imaging

Magnetic resonance imaging was performed 9 days after tumour implantation (before drug administration) and after the second injection of radiolabeled phenylalanine at day 18 as well as possibly at the day of scarification, using a 2.4-Tesla small animal magnetic resonance tomograph (Brucker Biospec 2.4, Karlruhe, Germany). This system was equipped with a rat coil to hold the animal and transmit homogeneous signals. All rats were imaged while under chloral hydrate anaesthesia (250 mg/kg, i.m.). Multiple axial and coronal images (T1- and T2-weighted) were acquired for 20 min without contrast media. The parameters used were: T1-weighted (TR=100 msec, TE=6.5 msec, flip angle 30°, FOV=2×2 cm, 256×128×64 matrix) and T2-weighted (TR=500 msec, TE=17.5 msec, 1 acquisition, RARE factor 16, FOV=2×2 cm, 256×256×32 matrix, slap-thickness 16 mm).

EXAMPLE 10

Gamma Camera Imaging

In separate experiments, whole body distribution of the tracer in tumor-bearing SCID mice and rats was visualized at different time points after intravenous administration of the corresponding radiopharmaceutical. Images were acquired over 20 min using a single-head gamma-camera (APEX SPX 4, Elscint Medical Systems, former Elscint Ltd, Haifa, Israel). The camera was equipped either with low energy, high resolution parallel-hole collimators (APC-45S, Elscint) or with high energy parallel pinhole collimators to assess photopeaks of corresponding radioisotopes.

EXAMPLE 11

Morphological and Histological Examinations

Human tumor cells grown on standard glass slides were fixed in 4% neutral buffered formalin and stained with the Giemsa method. The cell number was calculated in 10 consecutive high power fields (×40).

At autopsy of the rats and mice, besides the brains, other organs were harvested including the heart, lung, liver, spleen, kidney, skin, and colon. The brains were cut in coronal slices of about 2-3 mm thickness. All tissues from the animals were fixed in 4% neutral buffered formalin and embedded in paraffin wax. Sections were stained with hematoxylin-eosin and Verhoeff-van Gieson and examined histopathologically.

EXAMPLE 12

Statistical Analysis

The statistical significance of differences among experimental groups was determined by Student's t-test. A p-value less than 0.05 was considered significant.

EXAMPLE 13

Clinical Study with IPA-124

IPA was prepared, as described in example 3. A patient with a history as well as with clinical and structural imaging data (contrast enhanced MRI and/or CT) suggestive of a glioma, who was scheduled for surgical removal of the tumor, was asked for informed consent to undergo experimental IPA-124 PET imaging. The patient was injected with 50 MBq IPA-124, and subsequently dynamically imaged at 40-80 min and at 6 days post injection using a dedicated PET camera (Siemens ECAT-ART Scanner, Siemens-CTI, Knoxville, Tenn., USA). SPECT images were acquired using 3-degree angular steps. During a 360° rotation 120 projections were recorded into a 128*128 matrix, with an acquisition time of 40 s per image. Images were reconstructed using manufacturer's software. Anatomical co-alignment with MRI data was performed using HERMES software for nuclear medicine (Nuclear Diagnostics, Stockholm, Sweden) (FIGS. 12a and b). Tumor uptake was visually assessed by two adequately trained, independent nuclear medicine physicians. The patient was operated on day 2 post injection. Post-operative images continue to show strong IPA uptake in projection to the resection margins corresponding to a large portion of tumor tissue which remained in situ. The study demonstrates that IPA-124 is retained in high activity concentrations by tumor tissue for prolonged periods, suitably for the sustained administration of therapeutic radiation doses and parallel PET imaging. Post-operative images were semiquantitatively analysed. A region of interest (ROI) was drawn over the area of increased IPA-124 uptake and compared to a mirrored reference ROI in the contralateral healthy hemisphere using the median sagittal plane as mirror plane (FIG. 12c). Activity concentration in the remaining tumor tissue exceeded activity in the reference region by a factor of 8.86 after 6 days. IPA-124 was well tolerated.

EXAMPLE 14

Clinical Study with IPA-131

IPA was prepared, as described in example 3. A patient with a history, as well as with clinical and structural imaging data (contrast enhanced MRI and/or CT) suggestive of a glioma was asked for informed consent to undergo experimental IPA-131 administration, including IPA-131 SPECT imaging. The patient was injected with 100 MBq IPA-131 and subsequently imaged at 30 min and at 26 h post injection using a Hawkeye dual head SPECT camera (General Electrics Medical Systems, Uppsala, Sweden) with high energy collimator, and iterative reconstruction for cerebral (FIGS. 13a and b) and whole body (FIGS. 13c and d) imaging. SPECT images were acquired using 3-degree angular steps. During a 360° rotation 120 projections were recorded into a 128*128 matrix, with an acquisition time of 40 s per image. Images were reconstructed using manufacturer's software. Tumor uptake was visually assessed by two adequately trained, independent nuclear medicine physicians. The study demonstrates that IPA-131 is not only taken up but also retained by glioma tissue which renders it suitable for the sustained administration of therapeutic radiation doses and parallel SPECT imaging. IPA-131 was well tolerated.

EXAMPLE 15

Results and Discussion

In Vitro Studies

FIGS. 1-2 show examples of uptake kinetic of a radioiodinated L-phenylalanine in various tumor cell lines. As shown, the radiolabeled L-phenylalanines exhibit high uptake in human tumor cells with a continuous increase over the investigation time. This result provides evidence of the high affinity of the proposed radiopharmaceuticals for human tumors, including the human malignant gliomas, prostate and breast cancer.

Figure 3:
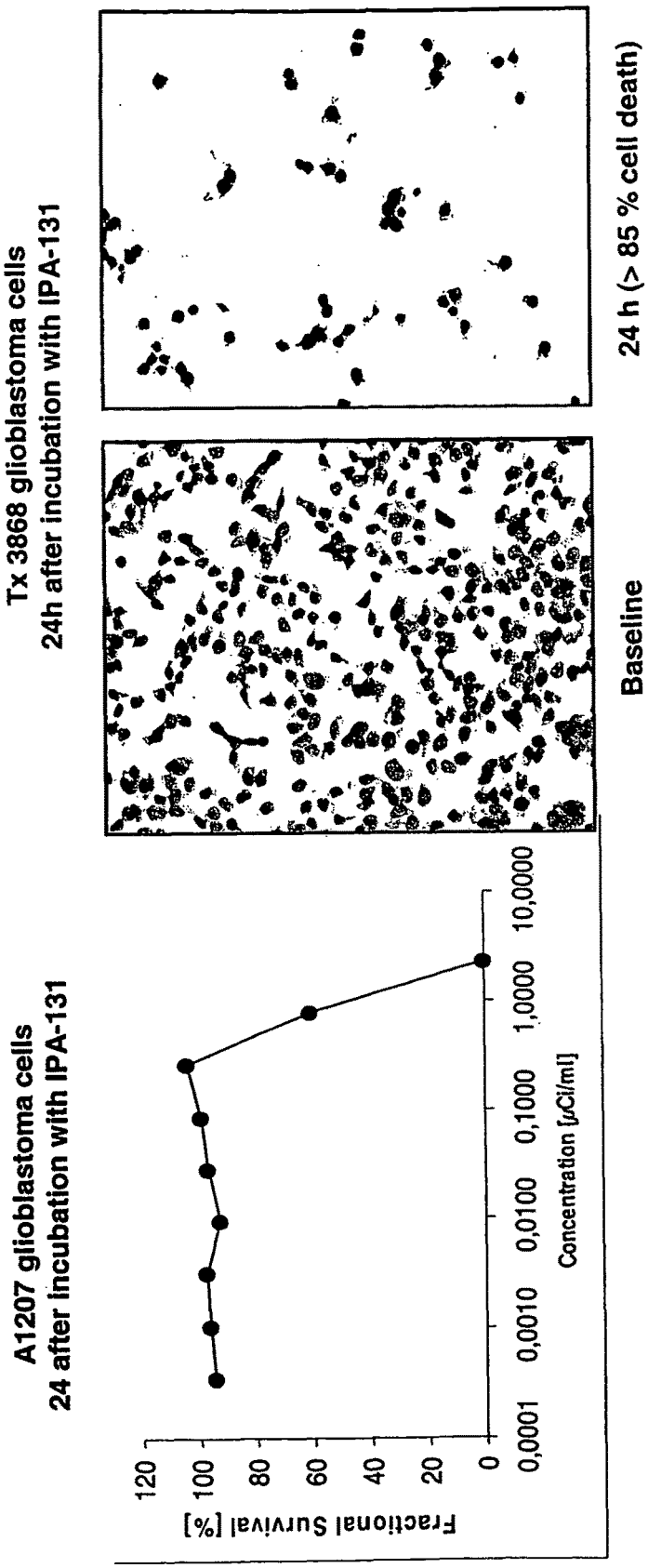
Figure 4:
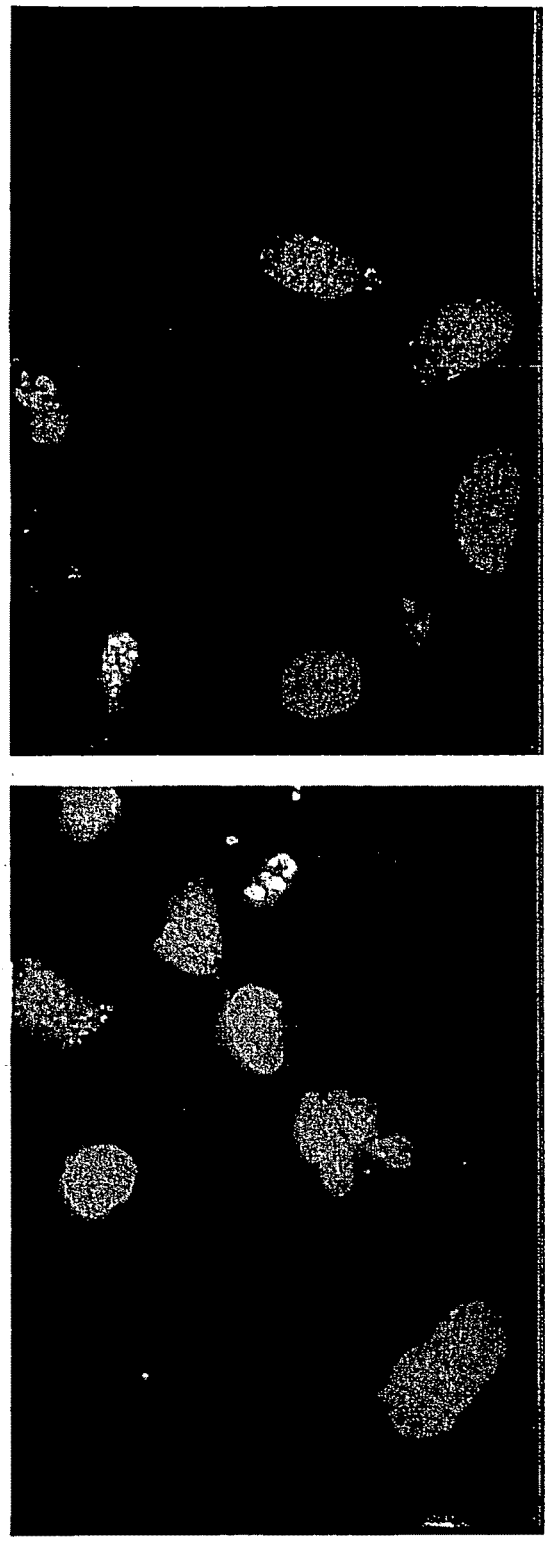

After 24 hours exposure of the primary human glioma cell lines with IPA-131, the cell count was clearly reduced (FIG. 3). Tx 3868 showed less than 22%, and T5135<20% cell survival rate after exposure with 1 µCi/ml IPA-131 compared to parallel grown cell cultures without exposure. The surviving cells contained only sparse cytoplasm, the nuclei were shrunken and contained clumped chromatin. Cytologically, the mode of cell death was apoptosis as the remaining tumour cells contained only sparsely cytoplasm and apoptotic bodies, in other cells the nuclei were shrunken and contained condensed chromatin.

Identical results were obtained with AtPA-211 and BrPA-77 in glioma, pancreas, prostate and breast cancer cells in vitro.

Flow-cytometric analyses of stained cells after treatment with IPA-131, BrPA-77 or AtPa-211 show a dose dependent induction of primary necrosis and apoptosis, which was more significant than that caused by external irradiation, even with 15 Gy (FIG. 4a-b). This results suggests a high potential of the beta-, alpha-, and Auger electron-emitting L-phenylalanines for human tumors, especially for malignant gliomas.

Animal Studies

Successful tumour implantation was observable non-invasively and clinically. FIG. 5 illustrates the experimental design to validate IPA-131 endoradiotherapy in rats with orthotopically implanted rat and human gliomas.

Figure 7:
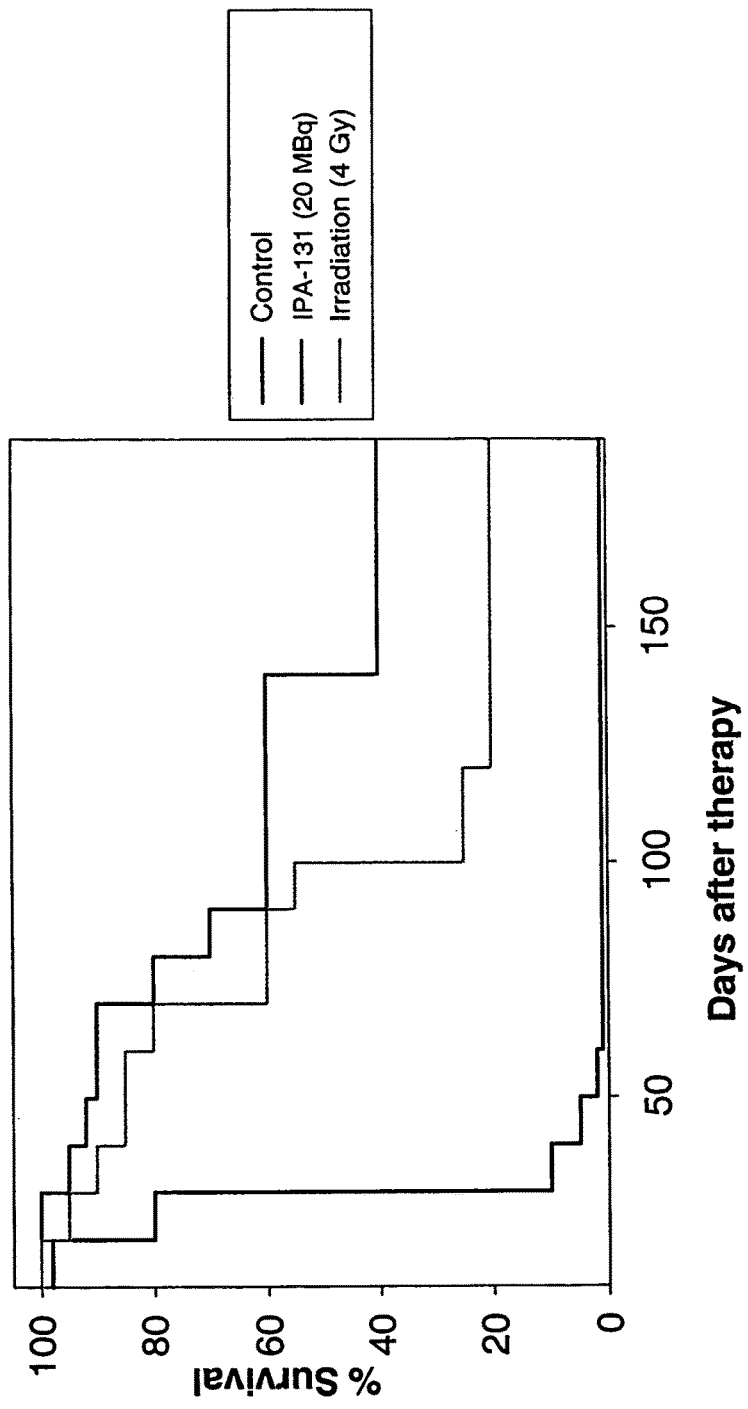
Figure 8:
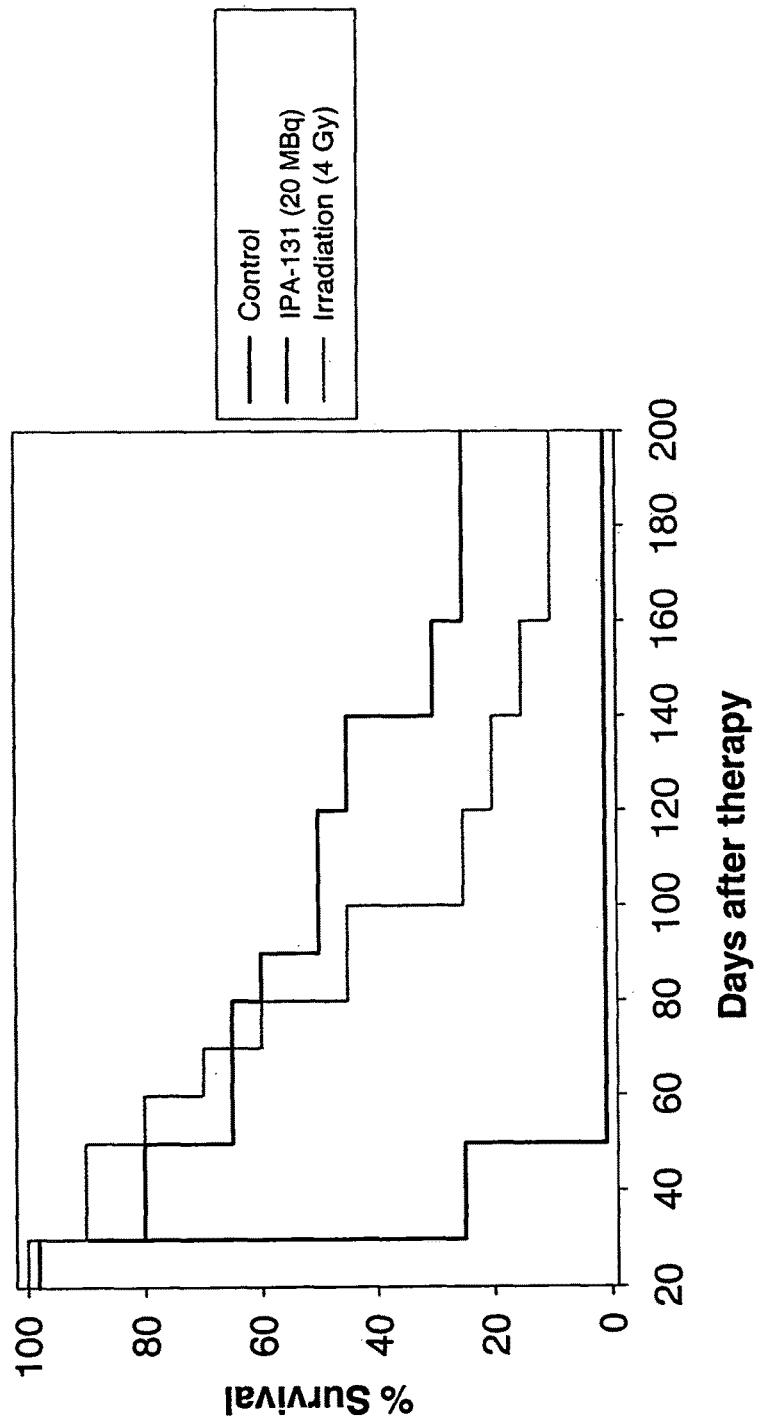
Figure 9:
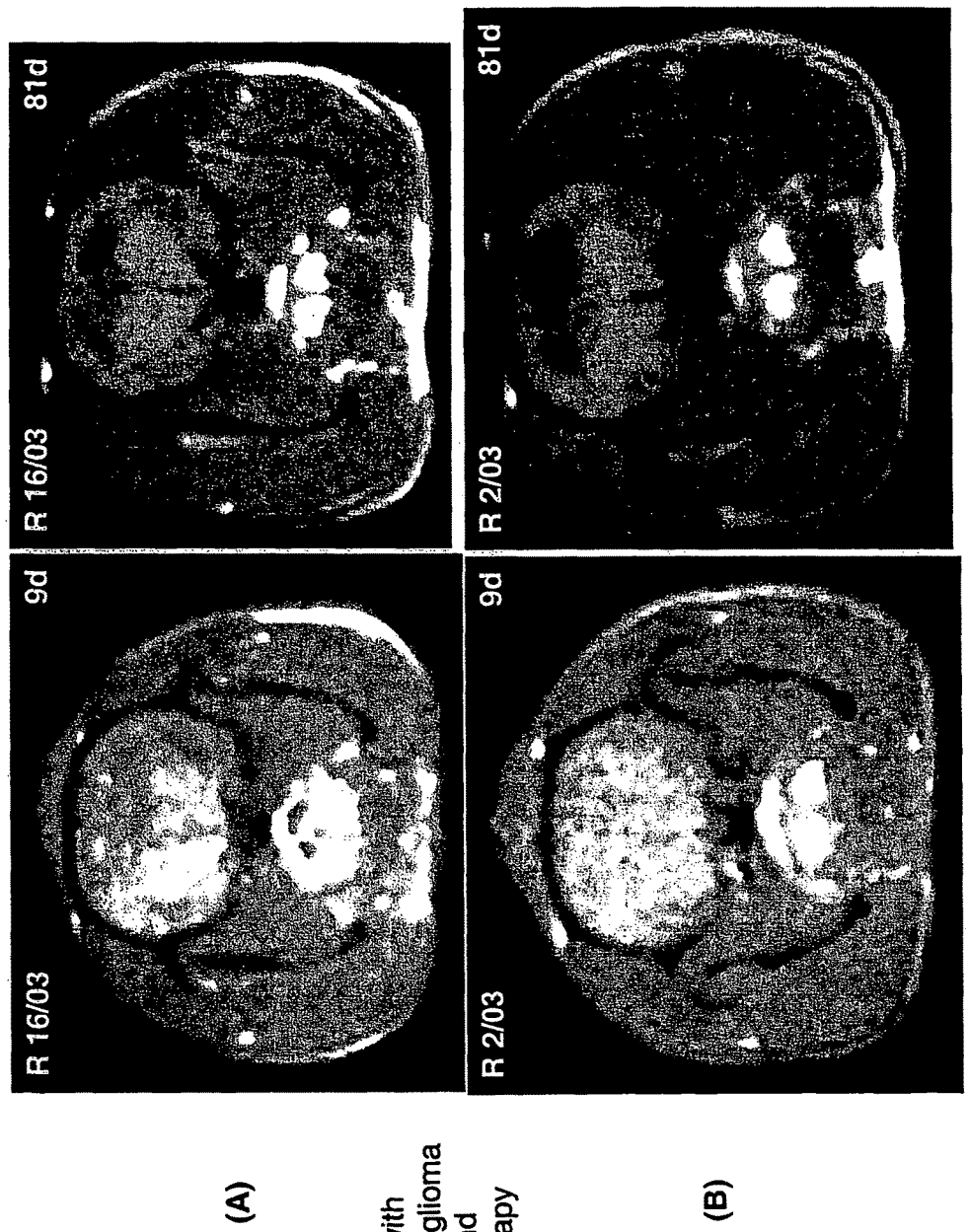
Figure 10:
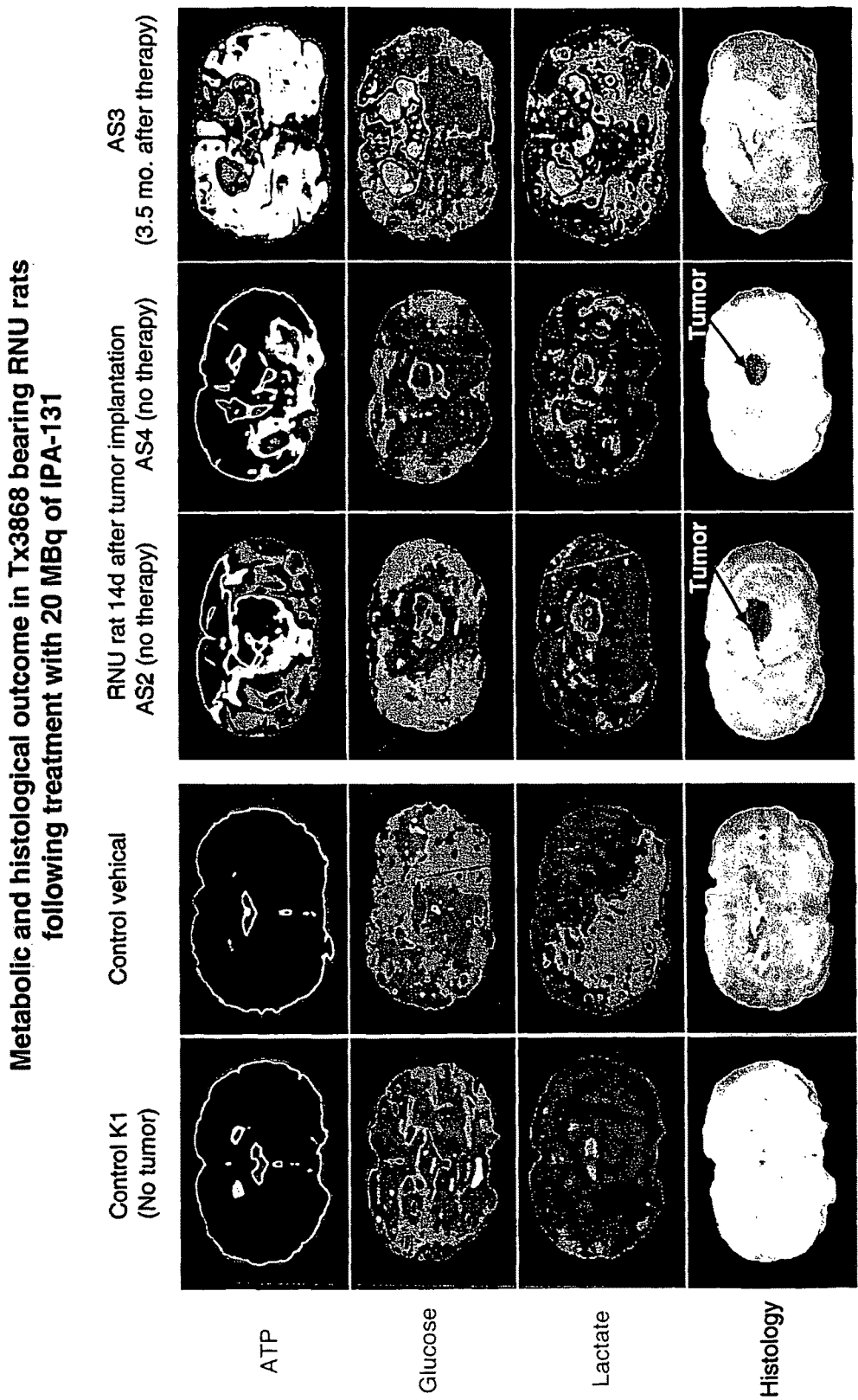
Figure 11:
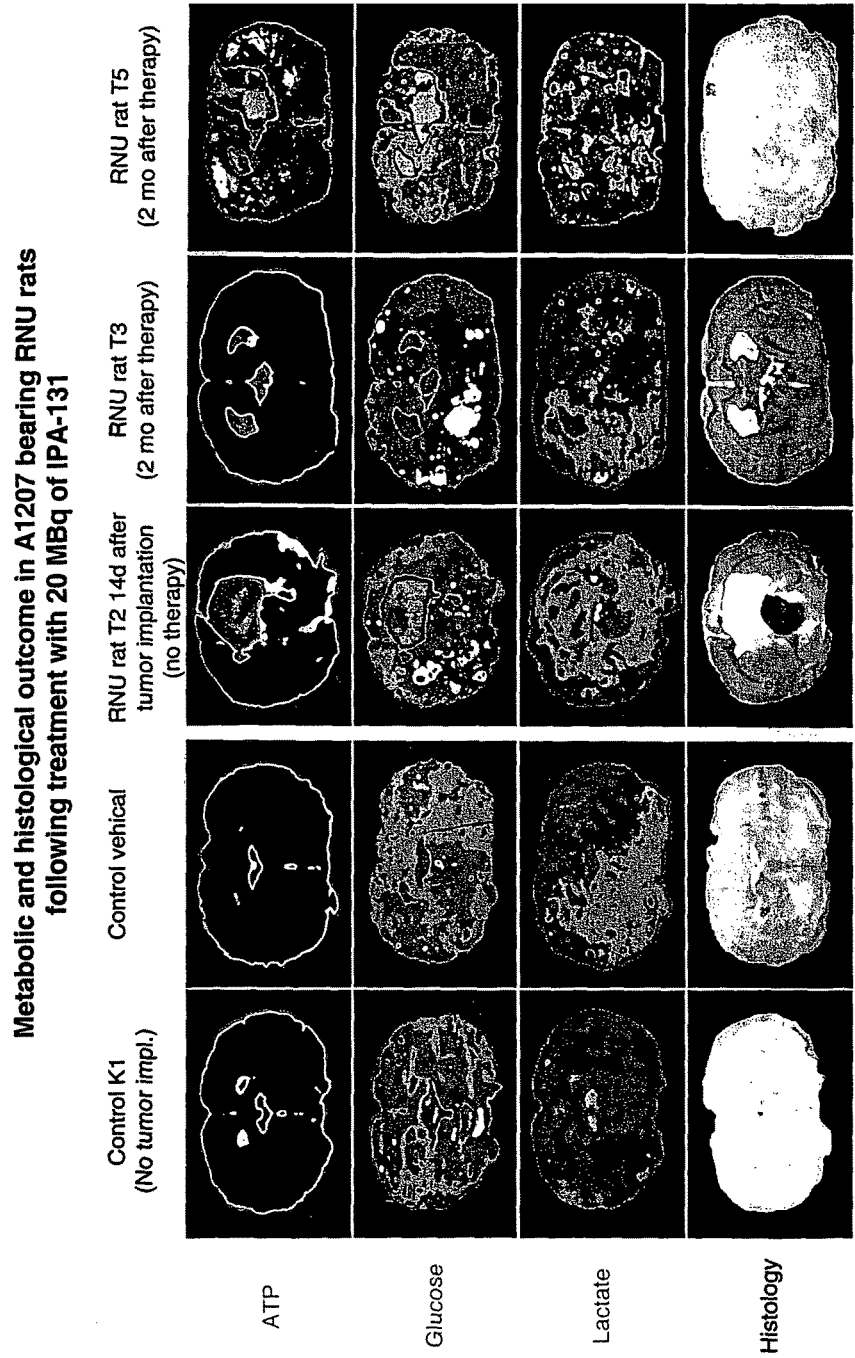
Figure 12:
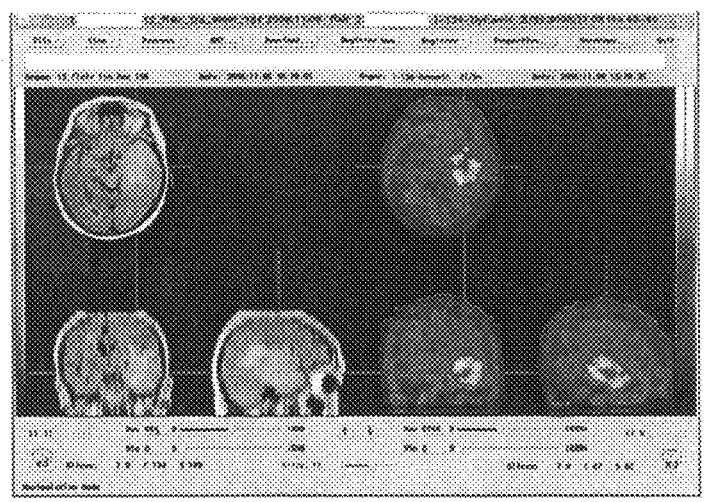
Figure 12:
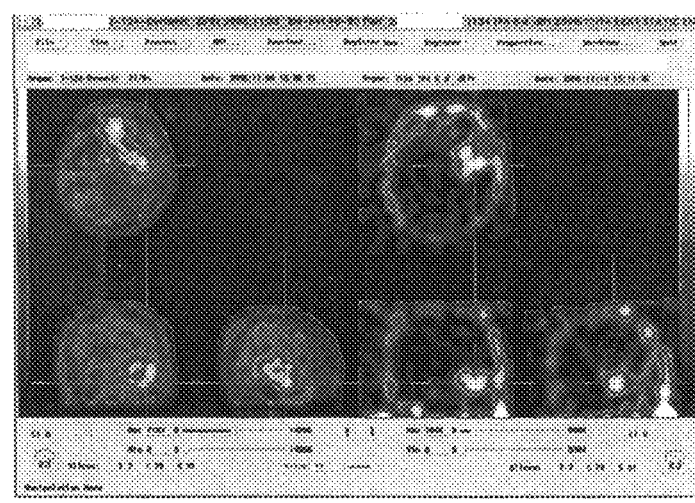
Figure 12:
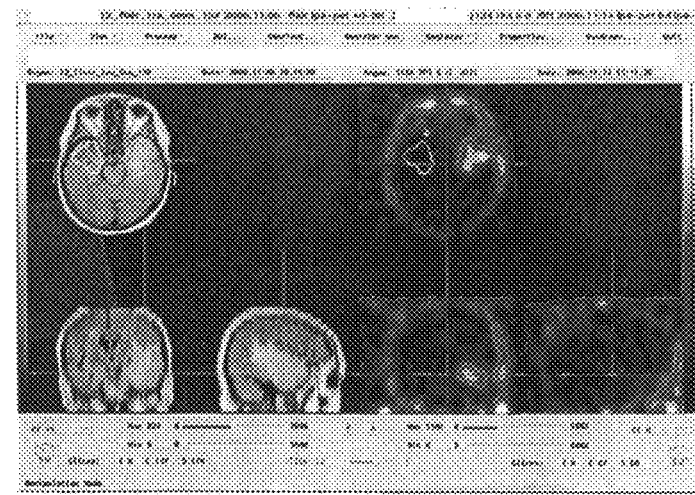
Figure 13A:
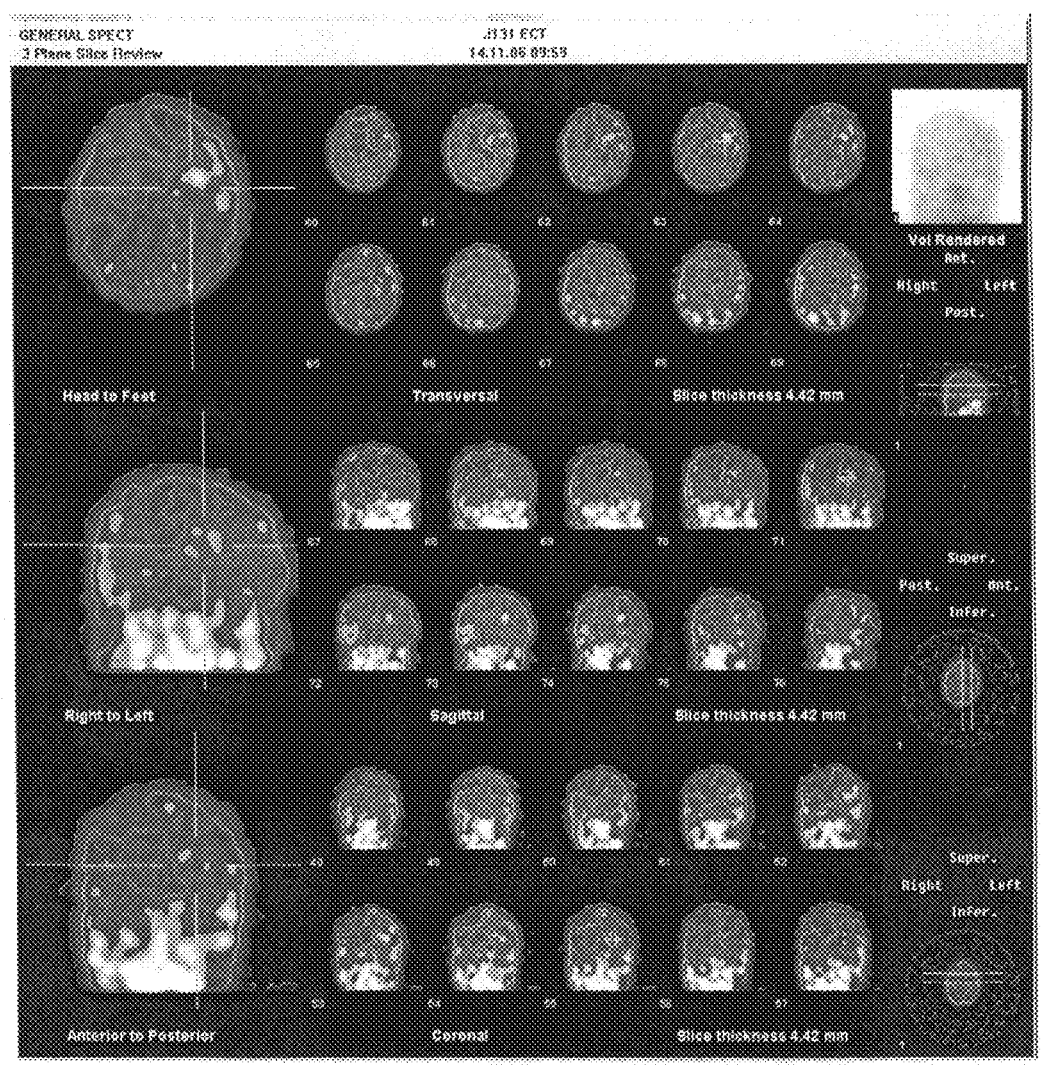
Figure 13B:
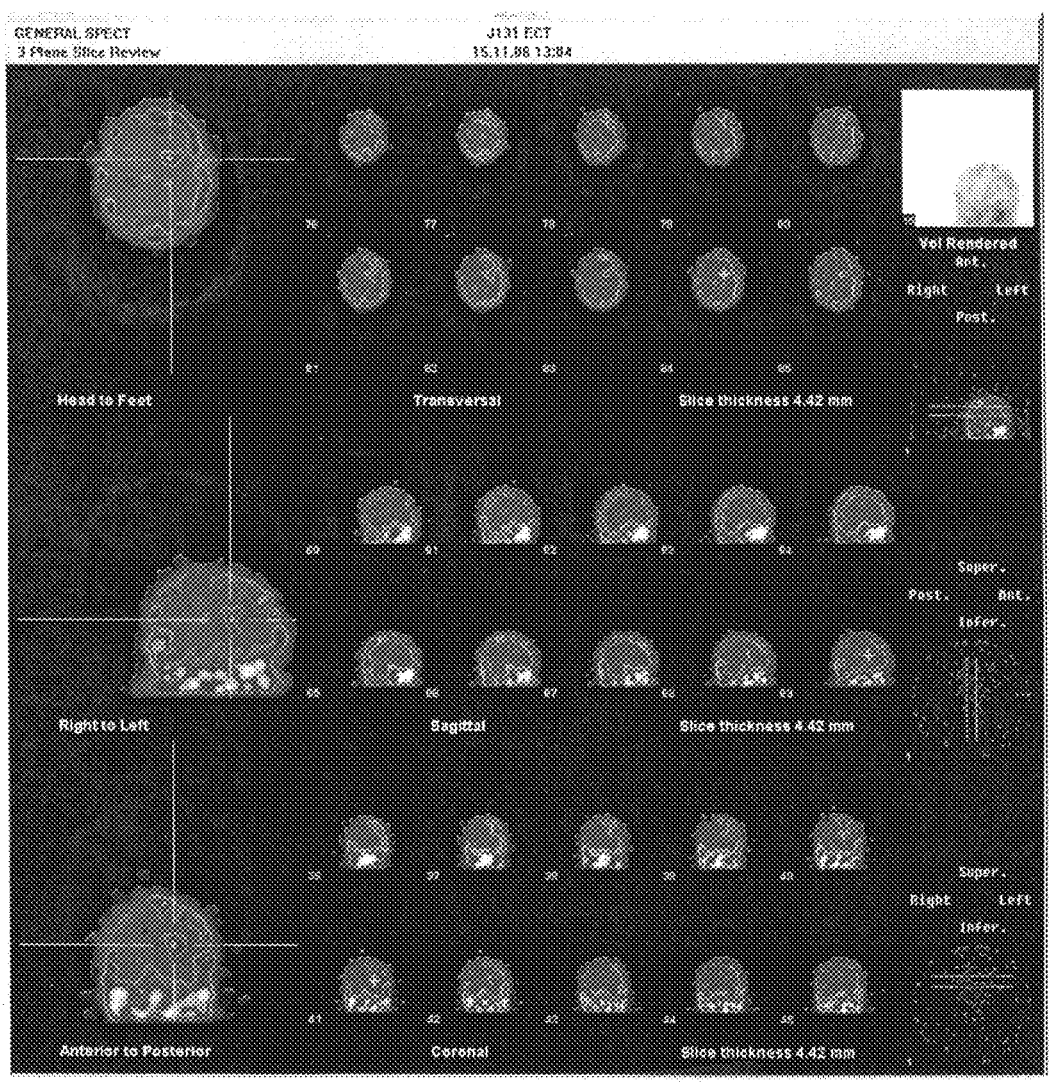
Figure 13C:
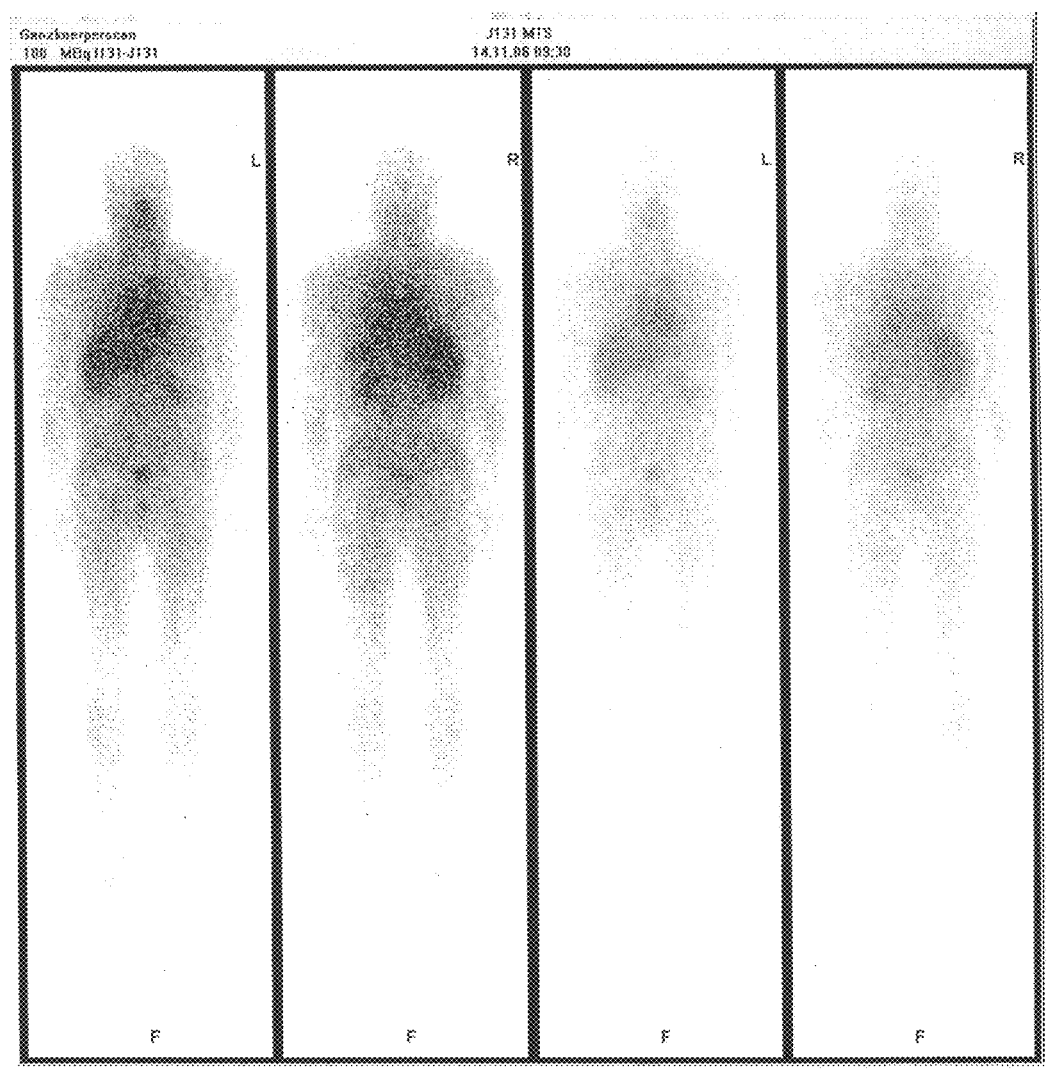
Figure 13D:
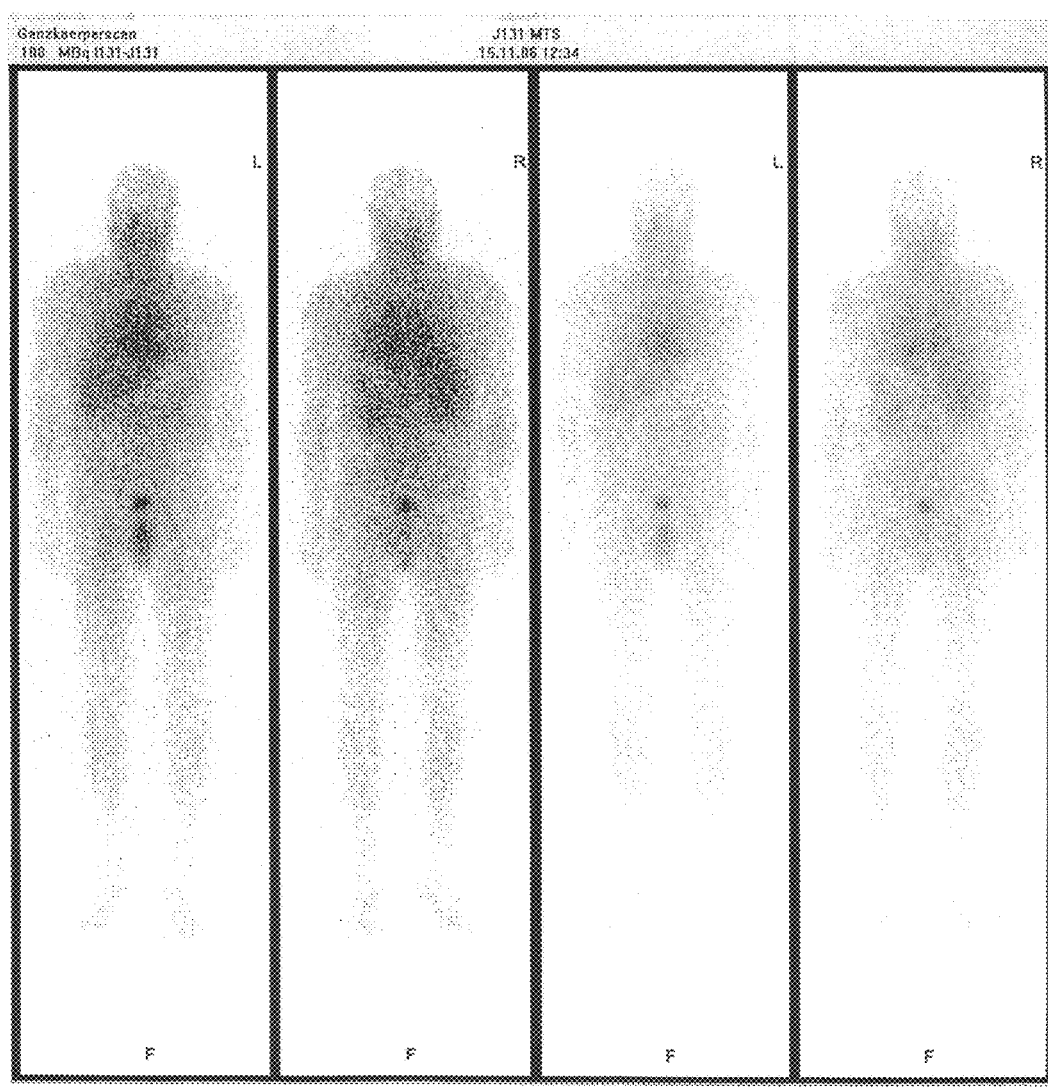

FIGS. 6-11 attested the efficacy of IPA-131 in the treatment of gliomas after systemic administration. In all glioma models the survival time of treated rats was significantly increased. According to the Kaplan-Meier analysis rats treated with IPA-131 not only survived longer than animals of the control group but showed a significantly longer survival than those treated by maximum tolerable doses of external irradiation (FIG. 7-8-9). Moreover, there were no adverse therapy-related events and no toxic effects were observed clinically. All survived C6-glioma rats were sacrificed 81 days after implantation at which time Kaplan-Meier survival curves showed significant longer survival of the treated animals group (p=<0.05), and no tumour was demonstrable with MRI. The long term surviving treated animals showed enlarged ventricles and no evidence of space occupying tumour, individual animals had demonstrable substance defects at the site of tumour implantation, furthermore, the subgaleal tumours had disappeared (FIG. 9). Besides underlying brain tissue there were groups of macrophages, occasional multinuclear giant cells of foreign body type, small calcifications, and focal infiltrates of lymphocytes. Furthermore, there were also pleomorphic astrocytic cells i.e. individual residual tumour cells or reactive astrocytes.

Autopsy proved that untreated animals died as a consequence to the presence of orthotopic gliomas. The other animals that died despite treatment showed the presence of orthotopic glioma cells. Histomorphologically, these tumours did not differ from those of untreated animals. All tumours were composed of pleomorphic cells, varying in size and with abundant eosinophilic cytoplasm. The vesicular nuclei often contained nucleoli. All tumours showed necrosis with pseudopalisading of nuclei. The tumour cells form a solid nodule at the site of implantation and diffuse spread of the tumour cells at the border to preexisting brain tissue. Frequent findings also include spread along the Virchow-Robin spaces, the ventricles, and the subarachnoid space.

One discussed problem of systemically administered IPA-131 consists in the radiation dose which does not reach the target cells, but the whole body and susceptible organs like bone marrow, the liver, the urogenital system, and of course the thyroid gland. Liver and kidneys of the treated animals did not show any histomorphological abnormality and no animal had clinical signs of malfunction of any organ as no side effects were observed clinically. No seizures were observed. In addition, the radiation doses estimated based on previous biodistribution studies in rats and in man, indicate that the use of the proposed L-phenylalanine derivatives should not result in a radiation dose superior to that determined in common radioimmunotherapy, and external irradiation [4, 19, 20].

Human Studies

Successful tumor targeting of human gliomas of different histological grades could be demonstrated for several embodiments of the invention, namely IPA-124 and IPA-131, which provides evidence that the tumor targeting effect of the radiolabelled phenylalanines is not dependent on the nuclide used for the labelling. This is further substantiated by the reference example showing IPA-123 targeting of human gliomas. Using IPA-124, which does in addition to its therapeutic beta irradiation possess a positron emission allowing for quantitative PET imaging, it was demonstrated that labelled phenylalanines can remain for prolonged periods in tumor tissue following initial uptake, which forms the basis for their therapeutic effect as described in this invention. In addition, it could be demonstrated that surgical therapy of glioma may inadequately underestimate the true extent of disease and thus emphasizes the need for an innovative medical therapy.

REFERENCE EXAMPLE

Clinical Studies with IPA-123

IPA was prepared, as described in example 2. Patients with a history as well as with clinical and structural imaging data (contrast enhanced MRI and/or CT) suggestive of a glioma were asked for informed consent to undergo experimental IPA-123 SPECT imaging. Patients were injected with 250 MBq IPA-123, and subsequently imaged at 30 min, 3 h and, where possible, 24 h post injection, using a triple head SPECT camera (Siemens Multi-SPECT III, Erlangen, Germany) with low energy high resolution (LEHR) collimator and iterative reconstruction for cerebral (FIG. 14) imaging. Whole body imaging (FIG. 15) was performed using a Hawkeye dual head SPECT camera (General Electrics Medical Systems, Uppsala, Sweden) with high energy collimator, and iterative reconstruction at 0 min, 1 h and 3 h after injection of 250 MBq IPA-123. SPECT images were acquired using 3-degree angular steps. During a 360° rotation 120 projections were recorded into a 128*128 matrix, with an acquisition time of 40 s per image. Images were reconstructed using manufacturer's software. Anatomical co-alignment with MRI data was performed using HERMES software for nuclear medicine (Nuclear Diagnostics, Stockholm, Sweden). Tumor uptake was visually assessed by two adequately trained, independent nuclear medicine physicians. In discordant cases, a consensus rating was agreed upon. 86% of patients with histologically confirmed tumor show IPA-123 uptake. This reference example serves to show that L-phenylalanine, independently of which isotope it is conjugated to, is able to cross the cross the blood-brain barrier and can accumulate specifically in malignant neoplasias.

All patients who were investigated gave their informed consent in accordance with the applicable laws and regulations.

In conclusion, our approach provides measurable efficacy in a preclinical brain tumour model of a novel treatment for this devastating tumour type that does not share the toxicity of conventional cancer therapies. Furthermore, our result suggests that the new radiolabeled L-phenylalanines may be a promising tracer for brain tumour therapy in humans, and might turn out to be a very effective diagnostic and therapeutic tool for various types of tumours.

REFERENCES

1. DeAngelis L M. Brain tumors. N Engl J Med 344: 114-123, 2001.
2. Black P M. Brain tumors. N Engl J Med 324: 1555-1564, 1991.
3. Kleihues P, Burger P C, Collins V P, Newcomb E W, Ohgaki H, Cavenee W K: Astrocytic tumours. Oligodendroglial tumours and mixed gliomas. In: Pathology and genetics of tumours of the nervous system (Kleihues P and Cavenee W K, eds). Lyon, IARC Press, 2000, pp 9-69.
4. Nieder C, Andratschke N, Wiedenmann N, et al. Radiotherapy for high-grade gliomas. Does altered fractionation improve the outcome? *Strahlenther Onkol* 180:401-407, 2004.
5. DeAngelis L M, Burger P C, Green S B, Cairncross F G. Malignant gliomas: who benefits from adjuvant chemotherapy. Ann Neurol 44: 691-695, 1998.
6. Riva P., Franceschi G, Riva N, Casi M, Santimaria M, Adamo M. Role of nuclear medicine in the treatment of malignant gliomas: the locoregional radioimmunotherapy approach. Eur J Nucl Med 27: 601-609, 2000.
7. Bowers G, He J, Schulz K, Olivarria G, Maneval D, Olson J J: Efficacy of adenoviral p53 delivery with SCH58500 in the intracranial 91 and RG2 models. Front Biosci 8: a54-61, 2003.
8. Perkins E, Calvert J, Lancon J A, Parent A D, Zhang J: Inhibition of H-ras as a treatment for experimental brain C6 glioma. Brain Res Mol Brain Res 1: 42-51, 2003.
9. Olzowy B, Hundt C S, Stocker S, Bise K, Reulen H J, Stummer W: Photoirradiation therapy of experimental malignant glioma with 5-aminolevulinic acid. J Neurosurg 97: 970-976, 2002.
10. Stander M, Naumann U, Wick W, Weller M: Transforming growth factor-beta and p-21: multiple molecular targets of decorin-mediated suppression of neoplastic growth. Cell Tissue Res 296: 221-227, 1999.
11. Diaz A Z. Assessment of the results from the phase I/II boron neutron capture therapy trials at the Brookhaven National Laboratory from clinician's point of view. J Neur Oncol 62: 101-109, 2003.
12. McDermott M W, Sneed P K, Gutin P H. Interstitial brachytherapy for malignant brain tumors. Sem Surg Oncol 14: 79-87, 1998.
13. Samnick S, Richter S, Romeike B F, Heimann A, Feiden W, Kempski O, Kirsch C M: Investigation of iodine-123-labelled amino acid derivatives for imaging cerebral gliomas: uptake in human glioma cells and evaluation in stereotactically implanted C6 glioma rats. Eur J Nucd Med 27: 1543-1551, 2000.
14. Hellwig D, Ketter R, Romeike B F, Sell N, Schaefer A, Moringlane J R, Kirsch C M, Samnick S: Validation of brain tumour imaging with p-[$^{123}$I]iodo-L-phenylalanine and SPECT. Eur J Nucd Med Mol Imaging 32: 1041-1049, 2005.
15. Warters R L, Hofer K G, Harris C R, Smith J M. Radionuclid toxicity in cultured mammalian cells: Elucidation of the primary site of radiation damage. Curr Top Radiat Res Quar 12: 389-407, 1977.
16. Zalutsky M R, Bigner D D: Radioimmunotherapy with alpha-particle emitting radioimmunoconjugates. Acta Oncol 35: 373-379, 1996.
17. Hofer K G, Keough G, Smith J M. Biological toxicity of Auger emitters: molecular fragmentation versus electron irradiation. Curr Top Radiat Res Quar 12: 335-354, 1977.
18. Stummer W, Stocker S, Novotny A, Heimann A, Sauer O, Kempski O, Plesnila N, Wietzorrek J, Reulen H J: In vitro and in vivo porphyrin accumulation by C6 glioma cells after exposure to 5-aminolevulinic acid. J Photochem Photobiol B 45: 160-169, 1998.
19. Brandes A, Soesan M, Florentino M: Medical treatment of high grade malignant gliomas in adults: an overview. Anticancer Res 11: 719-728, 1991.
20. Behr T M, Wormann B, Gramatzki M, Riggert J, Gratz S, Behe M, Griesinger F, Sharkey R M, Kolb H J, Hiddemann W, Goldenberg D M, Becker W: Low-versus high-dose radioimmunotherapy with humanized anti-CD22 or chimeric anti-CD20 antibodies in a broad spectrum of B cell-associated malignancies. Clin Cancer Res 5: 3304-3314, 1999.

The invention claimed is:

1. A method for the treatment of malignant neoplasia, the method comprising administering a L-phenylalanine conjugated to an alpha-, beta- or Auger-electron emitting isotope selected from the group consisting of bromine-76, bromine-77, bromine-82, iodine-124, iodine-125, iodine-131 and astatine-211 to a subject in the need thereof wherein the alpha-, beta- or Auger-electron emitting isotope is administered at an irradiation dose in the range of 10 to 400 MBq/kg body weight, wherein the malignant neoplasia is malignant glioma.

2. The method according to claim 1, wherein the glioma is selected from the group consisting of gliaoblastoma multiforme, anaplastic astrozytoma and oligoastrozytoma.

3. The method according to claim 1, wherein the conjugated L-phenylalanine is administered intravenously.

4. The method according to claim 1, wherein the irradiation dose of the alpha-, beta- or Auger-electron emitting isotope conjugated to the L-phenylalanine is administered as a single dose once or as a fractionated dose in 2 to 60 fraction doses.

5. The method according to claim 1, wherein the conjugated L-phenylalanine is 4-[$^{131}$I]iodo-L-phenylalanine or 4-[$^{211}$At]astatine-L-phenylalanine or 4-[$^{124}$I]iodo-L-phenylalanine (IPA-124).

6. The method according to claim 1, further comprising the step of a treatment of the subject by a concomitant therapy selected from the group consisting of a surgical therapy, a chemotherapy, a radiotherapy, an immunotherapy, a gene therapy, a vaccine therapy, an antisense nucleotide therapy, an intracavitary therapy, or a device-based treatment.

7. The method according to claim 6, wherein the concomitant therapy is a radiotherapy wherein the irradiation is started in a period of 0 to 7 days subsequent to the administration of the conjugated L-phenylalanine.

8. The method according to claim 1, wherein the subject is a human subject.

9. A method for the monitoring of the progress of a treatment of malignant neoplasia, wherein the malignant neoplasia is malignant glioma, the method comprising the steps:

(a) administering a L-phenylalanine conjugated to an alpha-, beta- or Auger-electron emitting isotope selected from the group consisting of bromine-76, bromine-77, bromine-82, iodine-124, iodine-125, iodine-131 and astatine-211 to a subject in the need thereof wherein the alpha-, beta- or Auger-electron emitting isotope is administered at an irradiation dose in the range of 10 to 400 MBq/kg body weight; and (b) localizing and/or dosimetrically measuring the conjugated L-phenylalanine in the subject by using a γ-camera.

10. The method according to claim 9, wherein the conjugated L-phenylalanine is localized and/or dosimetrically measured at least 0 to 7 days, preferably 0.5 to 48 h subsequent to its administration.

11. The method of claim 1, wherein the isotope is selected from bromine-76, bromine-77, bromine-82, iodine-124, iodine-131 and astatine-211.

12. The method of claim 1, wherein the conjugated L-phenylalanine is 3-[$^{125}$I]iodo-L-phenylalanine or 4-[$^{125}$I]iodo-L-phenylalanine.

* * * * *